(12) United States Patent  
Yamamoto

(10) Patent No.: US 8,412,503 B2  
(45) Date of Patent: Apr. 2, 2013

(54) SIMULATION SYSTEM OF CARDIAC FUNCTION, SIMULATION METHOD OF CARDIAC FUNCTION, SIMULATION PROGRAM OF CARDIAC FUNCTION, AND COMPOSITE MATERIAL SHEET

(76) Inventor: Shoji Yamamoto, Shiga (JP)

( * ) Notice: Subject to any disclaimer, the term of this patent is extended or adjusted under 35 U.S.C. 154(b) by 707 days.

(21) Appl. No.: 12/446,163

(22) PCT Filed: Oct. 16, 2007

(86) PCT No.: PCT/JP2007/070111  
§ 371 (c)(1),  
(2), (4) Date: Apr. 17, 2009

(87) PCT Pub. No.: WO2008/047766  
PCT Pub. Date: Apr. 24, 2008

(65) Prior Publication Data  
US 2010/0318326 A1    Dec. 16, 2010

(30) Foreign Application Priority Data

Oct. 17, 2006  (JP) ................. 2006-282913

(51) Int. Cl.  
*A61B 19/00* (2006.01)  
*G06F 17/50* (2006.01)  
*G06F 7/60* (2006.01)

(52) U.S. Cl. .......................... 703/11; 600/37

(58) Field of Classification Search ............ None  
See application file for complete search history.

(56) References Cited

U.S. PATENT DOCUMENTS  
2008/0120078 A1    5/2008  Hisada et al.

FOREIGN PATENT DOCUMENTS  
WO    00/46689    8/2000  
WO    2006/080349    8/2006

OTHER PUBLICATIONS

Amano, et al., "Model Generation Interface for Simulation of Left Ventricular Motion", The transactions of the Institute of Electronics, Information and Communication Engineers, Shadan Hojin The Institute of Electronics, Information and communication Engineers, May 2005, vol. J88-D-11, No. 5, pp. 943-953.  
Neilsen, et al., "Mathematical model of geometry and fibrous structure of the heart", American Journal of Physiology—Heart and Circulatory Physiology 260, USA, The American Physiology Society, 1991. H1365-H1378.  
Furuta, et al., "Pulsatile Cardiac Tissue Grafts Using a Novel Three-Dimensional Cell Sheet Manipulation Technique Functionally Integrates with the Host Heart, in Vivo", Circulation Research, Mar. 17, 2006, 98:705-712, U.S.A. American Heart Association, Inc.

*Primary Examiner* — Michael Borin  
(74) *Attorney, Agent, or Firm* — Hamre, Schumann, Mueller & Larson, P.C.

(57) ABSTRACT

To provide a simulation system of cardiac function utilizing a cardiac structure model which is generated based on an appropriate composite material view representing the myocardial tissue. A simulation system of cardiac function to predict a change in cardiac geometry using a cardiac structure model contains a material specification input part 11 to determine both connective tissue data and myocyte data, a geometry data input part 13 to input geometry data of three-dimensional geometry of a heart, and a cardiac-structure-model construction part 14 wherein a cardiac structure model assumes assembly of finite elements based on continuum data of three-dimensional geometry defined by geometry data and made of composite material containing matrix and reinforcement fiber, and possesses mechanical properties of reinforcement fiber reflecting mechanical properties of connective tissue data and mechanical properties of matrix reflecting mechanical properties of myocyte data. The simulation system also contains a simulation part 15 which predicts a change of geometry of the cardiac structure model produced by pressure load utilizing finite element method with computation.

13 Claims, 24 Drawing Sheets

Elastic Properties and Volume Fraction of Composite Components

|  | Young's Modulus (MPa) | Poisson's Ratio | Volume Fraction |
|---|---|---|---|
| Matrix | ~0.2 | 0.49 | 0.8 |
| Reinforcement Fibers | 100~ | 0.4 | 0.2 |

FIG. 5

| 3-layer model | Type 1 | Type 2 | Type 3 | Type 4 | Type 5 | Type 6 | Type 7 | Type 8 | Type 9 | Type 10 | Type 11 | Type 12 |
|---|---|---|---|---|---|---|---|---|---|---|---|---|
| Inner | 0 | +5 | +10 | +15 | +20 | +30 | +35 | +35.5 | +40 | +45 | +50 | +60 |
| Middle | 0 | 0 | 0 | 0 | 0 | 0 | 0 | 0 | 0 | 0 | 0 | 0 |
| Outer | 0 | -5 | -10 | -15 | -20 | -30 | -35 | -35.5 | -40 | -45 | -50 | -60 |

FIG. 10

| End-Systolic Parameters for Ellipsoid ||
|---|---|
| Major Radius | 65mm |
| Miner Radius | 20mm |
| Wall Thickness | 12mm |

FIG. 11

Composite configuration of myocardial tissue in 5-layer model for hearts

| 5-layer model | Control Hearts Connective Tissue (reinforcement fiber) | | | | Concentric Hearts Connective Tissue (reinforcement fiber) | | | | Eccentric Hearts Connective Tissue (reinforcement fiber) | | | |
|---|---|---|---|---|---|---|---|---|---|---|---|---|
| | Alignment (Angle, degree) | Space (μm) | Diameter (μm) | Volume Fraction | Alignment (Angle, degree) | Space (μm) | Diameter (μm) | Volume Fraction | Alignment (Angle, degree) | Space (μm) | Diameter (μm) | Volume Fraction |
| 1 (Endocardial) | +55 | 14 | 7 | 0.2 | +60 | 18 | 11 | 0.3 | +45 | 24 | 14 | 0.3 |
| 2 | +20 | 15 | 7 | 0.2 | +25 | 19 | 11 | 0.3 | +15 | 23 | 13 | 0.3 |
| 3 | 0 | 16 | 7 | 0.2 | 0 | 19 | 10 | 0.3 | 0 | 21 | 12 | 0.3 |
| 4 | −15 | 15 | 7 | 0.2 | −20 | 19 | 9 | 0.2 | −15 | 21 | 12 | 0.3 |
| 5 (Epicardial) | −40 | 14 | 7 | 0.2 | −45 | 16 | 7 | 0.2 | −45 | 26 | 14 | 0.3 |

FIG. 16

Pressure and geometry shape of left ventricle
in 5-layer model for heats

End-Systolic Parameters for Ellipsoid

|  | Controls | Concentric | Eccentric |
|---|---|---|---|
| Major Radius | 65 mm | 85 mm | 90 mm |
| Min or Radius | 20 mm | 30 mm | 30 mm |
| Wall Thickness | 12 mm | 24 mm | 18 mm |

Applied stress to Ventricular Cavity

|  | Controls | Concentric | Eccentric |
|---|---|---|---|
| Pressure | 20 KPa | 30 KPa | 20 KPa |

FIG. 17

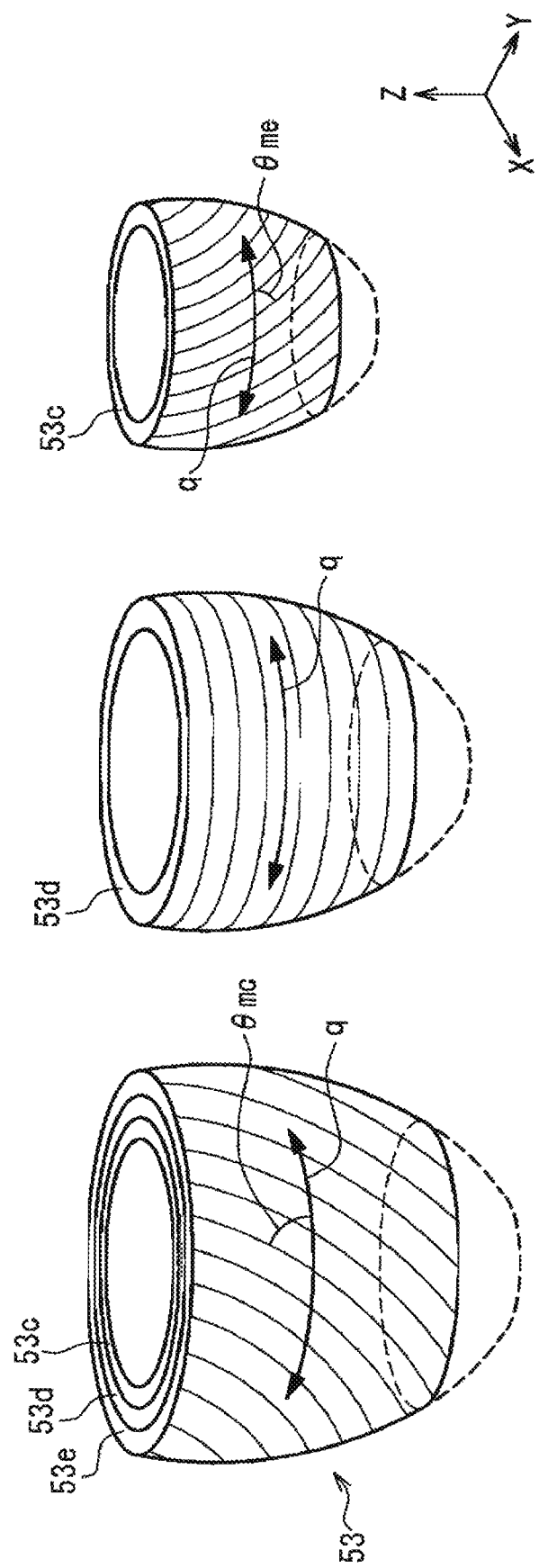

| 7-layer model | Control heart | | Diseased heart 1 | | Diseased heart 2 | |
|---|---|---|---|---|---|---|
| | Reinforcement fiber | | Reinforcement fiber | | Reinforcement fiber | |
| | (Orientation) | Volume fraction | (Orientation) | Volume fraction | (Orientation) | Volume fraction |
| Layer 1 (endocardial) | +50 | 0.2 | +50 | 0.2 | +45 | 0.2 |
| Layer 2 | +35 | 0.2 | +35 | 0.2 | +30 | 0.2 |
| Layer 3 | +15 | 0.2 | +15 | 0.2 | +10 | 0.2 |
| Layer 4 | 0 | 0.2 | 0 | 0.2 | 0 | 0.2 |
| Layer 5 | −15 | 0.2 | −15 | 0.2 | −10 | 0.2 |
| Layer 6 | −30 | 0.2 | −25 | 0.2 | −25 | 0.2 |
| Layer 7 (epicardial) | −45 | 0.2 | −30 | 0.2 | −30 | 0.2 |

FIG. 27

SIMULATION SYSTEM OF CARDIAC FUNCTION, SIMULATION METHOD OF CARDIAC FUNCTION, SIMULATION PROGRAM OF CARDIAC FUNCTION, AND COMPOSITE MATERIAL SHEET

FIELD OF THE INVENTION

The present invention relates to a simulation system of cardiac function to simulate a change in cardiac geometry utilizing a cardiac structure model which represents the myocardial tissue by data available in computation. The present invention also relates to a composite material sheet to support, supplement, and replace all or any part of heart.

BACKGROUND

It is a common observation in cardiac anatomy and histology that the myocardial tissue composing a heart is made of cardiomyocyte and connective tissue and possesses regular and characteristic tissue architectures. The cardiomyocytes are rod shaped, exhibiting fiber-like alignments, and are found embedded in the connective tissues mainly composed of collagen within the myocardial tissue. It is perceived that thin sheets of the myocardial tissue possessing such architectures are laminated and compose a cardiac wall.

Myocardial tissue architectures have been examined in relation to mechanical properties of myocardium as well as a cardiac function. For example, there has been a report of a simulation method to predict a change in ventricular geometry by finite element analysis, utilizing a cardiac structure model wherein the ventricular geometry and cardiomyocytic orientation are presented by data available in computation (example; see non-patent reference 1).

However, in the conventional methods, there is no example of cardiac structure model which contains an appropriate view of a composite material based on a detailed examination of material specifications of cardiomyocyte and connective tissue. Thus the myocardial tissue has not been fully elucidated in relation to the cardiac function.

Non-patent reference 1: P. M. F. Nielsen and other three co-authors. "Mathematical model of geometry and fibrous structure of the heart", American Journal of Physiology—Heart and Circulatory Physiology 260, USA, The American Physiology Society, 1991, H1365-H1378

SUMMARY OF THE INVENTION

Therefore the present invention aims to provide a simulation system of cardiac function utilizing a cardiac structure model which contains an appropriate view of a composite material based on the detailed examination of material specifications of cardiomyocyte and connective tissue, and a composite material sheet to support all or any part of heart which is made of an appropriate composite material.

A simulation system of cardiac function of the present application simulates a change in ventricular geometry by utilizing a cardiac structure model which represents a heart made of the myocardial tissue comprising both myocyte and connective tissue as continuum data of a composite material containing both matrix and reinforcement fiber. The simulation system includes a material specification input part to input both connective tissue data representing mechanical property of the connective tissue within the myocardial tissue and myocyte data representing mechanical property of the myocyte within the myocardial tissue, a geometry data input part to input geometry data of three-dimensional geometry of all or any part of the heart, a cardiac-structure-model construction part to generate the cardiac structure model that represents all or any part of the heart as an assembly of finite elements based on the continuum data of the three-dimensional geometry made of the composite material containing the matrix and the reinforcement fiber, and set the mechanical property represented by the myocyte data as a mechanical property of the matrix and set the mechanical property represented by the connective tissue data as a mechanical property of the reinforcement fiber, and a simulation part to calculate a change in geometry of the heart represented by the cardiac structure model under a pressure load by utilizing finite element method with computation.

The cardiac-structure-model construction part generates the cardiac structure model formed as the three-dimensional geometry represented by the geometry data made of a composite material. The cardiac structure model possesses both mechanical properties of the reinforcement fiber reflecting those of the connective tissue data and mechanical properties of the matrix reflecting those of the myocyte data. That is, the cardiac structure model is made of a composite material in which the connective tissue of the myocardial tissue is regarded as unidirectional reinforcement fiber of the composite material and the myocyte of the myocardial tissue is regarded as matrix of the composite. Thus the cardiac-structure-model construction part can provide the cardiac structure model which appropriately characterizes the myocardial tissue as a composite material.

The conventional methods of simulation of cardiac function have never utilized any cardiac model with an appropriate perspective of composite material in which, based on the mechanical properties of myocardial tissue components, a connective tissue component within the myocardial tissue is assigned as reinforcement fiber of the composite material composing a cardiac model and a cardiomyocyte component within the myocardial tissue is assigned as matrix of the composite material. The inventor examined the mechanical properties of connective tissue and cardiomyocyte within the myocardial tissue, and found that, based on such examination, it was appropriate to assign the connective tissue as reinforcement fiber element of a composite material and the cardiomyocyte as matrix element. The simulation part proceeds a calculation for a change in cardiac geometry utilizing the cardiac structure model based on a composite material perspective of the myocardium in which connective tissue and cardiomyocyte are appropriately assigned as reinforcement fiber and matrix elements of the composite material, respectively. Thus a simulation of a change in cardiac geometry, particularly the simulation reflecting the mechanical properties of connective tissue and cardiomyocyte within the myocardial tissue, becomes available.

The 'connective tissue', mentioned above, refers to the interstitial tissue which occupies tissue spaces between cardiomyocytes. The connective tissue includes both endomysium which surrounds individual cardiomyocytes and perimysium which demarcates bundles (groups) of cardiomyocytes. The connective tissue may contain collagen fiber as its major component as well as other tissue components.

A 'composite material' is a material made of two or more material elements which have distinctive physical properties. A 'composite material' can possess its material properties superior to or different from the original material properties of individual material elements.

In the simulation system of cardiac function of the present invention, it is preferable that the material specification input part inputs the connective tissue data including a value for the Young's modulus of the connective tissue and the myocyte data including a value for the Young's modulus of the myocyte, and the value for the Young's modulus of the connective tissue is as large as one hundred times or more of the value for the Young's modulus of the myocyte.

The inventor compared the elastic properties of cardiomyocyte and connective tissue, and examined any difference in mechanical properties between the two tissue components by experimental observations as well as logical presumptions. Such comparative examinations have revealed that, in a heart of non-contracting condition, the Young' modulus of connective tissue material is quite larger than that of cardiomyocyte material, and more specifically that the value for the Young' modulus of connective tissue material is as large as one hundred times or more of that for the Young' modulus of cardiomyocyte. That is, the inventor has found that the myocardial tissue possesses material properties consistent with those of FRR (fiber reinforced rubber), a particular composite material which is characterized by a large difference in values for the Young' modulus between reinforcement fiber and matrix. In the preferred aspect of the present invention, by inputting the values for the Young' modulus of connective tissue as large as one hundred times or more of those for the Young' modulus of cardiomyocyte in a material specification input part, a cardiac-structure-model construction part is able to provide a cardiac structure model which comprises the composite material properly reflecting the difference in elastic properties between cardiomyocyte and connective tissue of the myocardium. That is, a cardiac-structure-model construction part is able to provide a cardiac structure model containing the cardiac wall of a composite material characterized by the material characteristics of FRR. Accordingly it is possible to provide a cardiac structure model comprising the composite material which better represents the material properties of actual myocardial tissue than the traditional cardiac structure models do in the conventional methods of simulation of cardiac function.

In the simulation system of cardiac function of the present invention. It is preferable that the cardiac-structure-model construction part generates assembly of finite elements based on the continuum of three-dimensional geometry made of unidirectional fiber-reinforced rubber composite material containing both the matrix made of rubber and the unidirectional reinforcement fiber, and the mechanical property of the unidirectional reinforcement fiber is defined by the property of the connective tissue represented by the connective tissue data and the mechanical property of the matrix is defined by the property of myocyte represented by the myocyte data within the cardiac structure model.

As described above, the inventor has found that the myocardial tissue possesses the material properties consistent with those of FRR. Thus the cardiac-structure-model construction part is able to provide a particular cardiac structure model representing the material properties of myocardial tissue consistent with those of FRR by constructing a cardiac structure model which assumes assembly of finite elements based on continuum data of the three-dimensional geometry made of unidirectional fiber reinforced rubber composite material.

It is preferable that the simulation system of cardiac function in the present invention further includes a construction data input part to input myocardial tissue construction data including a volume fraction of the connective tissue within the myocardial tissue, and the cardiac-structure-model construction part determines a volume fraction of the reinforcement fiber within the composite material composing the cardiac structure model based on the volume fraction of the connective tissue within the myocardial tissue.

Values for a volume fraction of connective tissue within the myocardial tissue are among tissue morphological data (morphometry) which are obtained by morphological observations of the myocardial tissue. Using the morphometry data of a volume fraction of connective tissue, the cardiac-structure-model construction part is able to provide the cardiac structure model wherein a prevalence of reinforcement fibers within a composite material reflects the volume fraction of connective tissue within the myocardial tissue. Thus, utilizing the cardiac structure model in the present invention, a simulation of cardiac function which takes into consideration the morphometric information of myocardial tissue, a factor among those closely related to a cardiac function, becomes available.

It is preferable that the simulation system of cardiac function in the present invention further includes a construction data input part to input myocardial tissue construction data including cell diameter of the myocyte, and the cardiac-structure-model construction part determines a center-to-center distance of the reinforcement fibers within the composite material composing the cardiac structure model based on the cell diameter of the myocyte.

Values for the cell diameter of cardiomyocyte are among tissue morphological data (morphometry) which are obtained by morphological observations of the myocardial tissue. Using the morphometry data of cell diameter, a cardiac-structure-model construction part is able to provide a cardiac structure model wherein architecture of a composite material reflects the cell diameter of cardiomyocyte.

It is preferable that the simulation system of cardiac function in the present invention further includes a construction data input part to input myocardial tissue construction data including a value for volume fraction of the connective tissue within myocardial tissue and a value for cell diameter of myocyte, and the cardiac-structure-model construction part determines diameter of the reinforcement fiber within the composite material composing the cardiac structure model based on both the value for the volume fraction of the connective tissue within the myocardial tissue and the value for the cell diameter of the myocyte.

Using the morphometry data of a volume fraction of connective tissue and a cell diameter, the cardiac-structure-model construction part is able to provide a cardiac structure model wherein a diameter of reinforcement fiber of a composite material reflects both a value for the volume fraction of connective tissue within the myocardial tissue and a value for the cell diameter of cardiomyocyte.

It is preferable that the simulation system of cardiac function in the present invention further includes a construction data input part to input myocardial tissue construction data including data to indicate orientations of longitudinal alignment of the cardiomyocyte and the cardiac-structure-model construction part generates a cardiac structure model that represents the heart wherein a ventricular wall of the heart is composed of multiple layers of curved sheets of the composite material and orientations of longitudinal alignment of reinforcement fiber within the composite material are defined in the each curved sheet according to the myocardial tissue construction data.

The myocardial tissue structure within a ventricular wall of actual heart can be modeled as a laminate architecture of multiple myocardial layers, each tangent to a ventricular surface. Orientations of longitudinal alignment of cardiomyocytes, as observed within the myocardial multiple layers at different positions along the transmural direction of a ventricular wall, change in direction from the inner to outer surface of the ventricle. The longitudinal alignments of cardiomyocytes are consistent with those of the connective tissue (mostly endomysium) which surround the cardiomyocytes. The transmural changes in direction of cardiomyocyte longitudinal alignment in the ventricular wall sometimes present distinctive characteristics between normal and diseased hearts, which are closely related to cardiac functions of different hearts.

The cardiac-structure-model construction part is able to provide a cardiac structure model wherein orientations of longitudinal alignment of reinforcement fiber of the composite material within individual sheets among laminated curved sheets reflect the data to indicate orientation of longitudinal alignment of the cardiomyocyte. Thus, using the cardiac structure model, there becomes available a simulation of cardiac function which reflects the change in orientation of longitudinal alignment of cardiomyocyte (along different wall-depths from the inner to outer surface of ventricle). The change in orientation of longitudinal alignment of cardiomyocyte is a factor among those closely related to a cardiac function.

In the simulation system of cardiac function in the present invention, it is preferable that the cardiac-structure-model construction part defines a ventricular wall of the heart that is composed of N (N is an odd number) layers of the curved sheets of the composite material, and the orientation of longitudinal alignment of reinforcement fiber in the central layer among the N layers of curved sheets is defined by the fiber orientation of ventricular circular muscle of the heart.

It is a common observation in cardiac anatomy that a layer defined as circular muscle of the ventricle exists at the middle of multiple myocardial layers composing the ventricular wall. In the circular muscle layer, cardiomyocytes and the connective tissues which surround individual cardiomyocytes are aligned along their longitudinal axes, both predominantly run in parallel to a short axis plane of a ventricular geometry model of ellipsoid of revolution. The cardiac-structure-model construction part, generating a cardiac structure model wherein the orientation of longitudinal alignment of reinforcement fiber in the central layer of N layers of curved sheets is defined in consistent with a fiber orientation of the ventricular circular muscle, is thus able to provide a particular cardiac structure model which closely represents the myocardial structure of ventricular wall in an actual heart.

In the simulation system of cardiac function in the present invention, it is preferable that the cardiac-structure-model construction part defines orientations of longitudinal alignment of the reinforcement fiber in individual curved sheets so that the orientations are in-plane within each curved sheet and yet vary among different curved sheets.

The cardiac-structure-model construction part generates the cardiac structure model wherein the orientations of longitudinal alignment of reinforcement fiber vary among different curved sheets, and thus are able to provide a particular cardiac structure model which reflects the change in direction, along different wall-depths from the inner to outer surface of ventricle, of orientation of cardiomyocyte longitudinal alignment in an actual heart.

In the simulation system of cardiac function in the present invention, it is preferable that the material specification input part inputs the value for Young's modulus of the myocyte as the myocyte data and the value for the Young's modulus of connective tissues as large as one hundred times or more of the value for the Young's modulus of the myocyte as the connective tissue data, and the cardiac-structure-model construction part defines the orientations of longitudinal alignment of the reinforcement fiber so that the orientations differ by angel value of a specific bias angle or its complement between at least one pair of adjacent curved sheets The material specification input part inputs, as the connective tissue data, the values for the Young's modulus of connective tissues as large as one hundred times or more of the values for the Young's modulus of cardiomyocyte. Thus, the cardiac-structure-model construction part is able to provide a particular cardiac structure model wherein a ventricular wall of the heart is composed of multiple layers of the curved sheets of composite material which is characterized by the material characteristics of FRR.

It is a common observation that a fiber-reinforced-rubber sheet with a 2-layers angle-ply architecture utilizing a specific bias angle possesses a characteristic mechanical properties. For example, an out-of-plain coupling (out-of-plain torsion) disappears in such fiber-reinforced-rubber sheet. The inventor has revealed that within the myocardial tissue of an actual heart, the myocardial tissue structures possess such characteristic mechanical properties which are attributed to the composite architectures utilizing a specific bias angle.

Given the myocardial tissue structures possessing the particular mechanical characteristics of fiber-reinforced-rubber sheet in an actual heart, the cardiac-structure-model construction part defines the orientations of longitudinal alignment of reinforcement fiber in individual curved sheets in a way so that the orientations between at least one pair of adjacent curved sheets differ in angle by value of a specific bias angle or its complement. The simulation part is thus able to proceed a calculation for a change in cardiac geometry which reflects the myocardial tissue composite architectures utilizing a specific bias angle.

It is preferable that the simulation system of cardiac function in the present invention further includes a sheet data input part to input sheet data representing a composite material sheet to support all or any part of the heart and including mechanical properties of a reinforcement fiber and a matrix within the composite material sheet, orientation of longitudinal alignment of the reinforcement fiber, and a shape of the composite material sheet, and the cardiac-structure-model construction part generates a cardiac structure model representing a continuum of the three-dimensional geometry represented by the geometry data configured with the composite material sheets characterized by the sheet data.

The cardiac-structure-model construction part generates the cardiac structure model made of the continuum of the three-dimensional geometry which is configured with the composite material sheets presented by the sheet data. Thus the cardiac-structure-model construction part is able to provide a cardiac structure model made of the heart configured with the composite material sheets, and a simulation part using such cardiac structure model is able to proceed a calculation to simulate a change of geometry of the cardiac structure model comprising composite material sheets which is produced by pressure load. Proceeding such calculation, a cardiac function can be examined in reference to the characteristics of composite material sheets which compose a cardiac structure model. To utilize the calculation date in designing composite material sheets also facilitates optimal designing of the composite material sheets which are used to improve impaired cardiac functions.

The composite material sheet in the present invention supports all or any part of the heart and comprises a lamina or a laminate of thin sheet made of a composite material which contains reinforcement fiber and matrix, and a value for the Young' modulus of the reinforcement fiber is as large as one hundred times or more of a value for the Young' modulus of the matrix.

A value for the Young' modulus of the connective tissue within the myocardial tissue is as large as one hundred times or more of a value for the Young' modulus of cardiomyocyte within the myocardial tissue. Given the comparative values of connective tissue and cardiomyocyte within the myocardial tissue, the composite material sheet wherein a value for the Young' modulus of the reinforcement fiber is as large as one hundred times or more of a value for the Young' modulus of matrix within the composite material possesses material characteristics consistent with those of the myocardial tissue. Thus a composite material sheet which comprises an appropriate composite material and supports all or any part of heart is provided.

It is preferable that the composite material sheet in the present invention comprises the laminate of a plural number of thin sheets made of a composite material containing unidirectional reinforcement fiber and matrix, and the plural number of thin sheets are laminated in a way so that orientations of longitudinal alignment of unidirectional reinforcement fibers, in-plane in individual thin sheets, yet vary among the sheets, and a difference in angel value of orientations between at least one pair of adjacent thin sheets is a specific bias angle or its complement between at least one pair of adjacent thin sheets.

The myocardial tissue structure within the ventricular wall of actual heart can be modeled as a laminate architecture of multiple myocardial tissue layers, each tangent to a ventricular surface. Orientations of longitudinal alignment of cardiomyocytes, as observed within the myocardial tissue layers at different transmural positions of the ventricle, change in direction. It is also found by the inventor, as already described above, that the myocardial tissue possesses material characteristics consistent with those of unidirectional fiber reinforced composite material wherein a value for the Young' modulus of the reinforcement fiber is as large as one hundred times or more of a value for the Young' modulus of matrix. In addition, the inventor found that, within the myocardial tissue of an actual heart, orientations of longitudinal alignment of cardiomyocytes within multiple tangential tissue layers of the ventricle present particular transmural changes which are characterized by values of a specific bias angle, and that the myocardial tissue architecture with such orientations of longitudinal alignment of cardiomyocytes is closely related to a cardiac function of heart.

The simulation method of cardiac function of the present invention simulates a change in ventricular geometry by computation. The simulation method utilizes the cardiac structure model to represent a heart made of the myocardial tissue comprising both myocyte and connective tissue as continuum data of a composite material containing matrix and reinforcement fiber. The simulation method includes a process to input connective tissue data representing mechanical property of the connective tissue within the myocardial tissue and myocyte data representing mechanical property of the myocyte within the myocardial tissue, a process to input geometry data of three-dimensional geometry of all or any part of the heart, a process to generate the cardiac structure model that represents all or any part of the heart as assembly of finite elements based on the continuum data of the three-dimensional geometry made of the composite material containing the matrix and the reinforcement fiber, and set the mechanical property represented by the myocyte data as a mechanical property of the matrix and set the mechanical property represented by the connective tissue data as a mechanical property of the reinforcement fiber, and a process to calculate a change in geometry of the heart represented by the cardiac structure model under a pressure load by utilizing finite element method with computation.

A simulation program of cardiac function in the present invention directs a computer to execute a simulation of a change in ventricular geometry. The simulation program utilizes a cardiac structure model to represent a heart made of the myocardial tissue comprising both myocyte and connective tissue as continuum data of a composite material containing matrix and reinforcement fiber. The simulation program directs the computer to execute a computation processing to input both connective tissue data representing mechanical property of the connective tissue within myocardial tissue and myocyte data representing mechanical property of the myocyte within the myocardial tissue, a computation processing to input geometry data of three-dimensional geometry of all or any part of the heart, a cardiac-structure-model construction part to generate the cardiac structure model that represents all or any part of the heart as an assembly of finite elements based on the continuum data of the three-dimensional geometry made of the composite material containing the matrix and the reinforcement fiber, and set the mechanical property represented by the myocyte data as a mechanical property of the matrix and set the mechanical property represented by the connective tissue data as a mechanical property of the reinforcement fiber, and a computation processing to calculate a change in geometry of the heart represented by the cardiac structure model under a pressure load by utilizing finite element method with computation.

The present invention is able to provide the simulation system of cardiac function utilizing the cardiac structure model which contains an appropriate view of the composite material and a composite material sheet which comprises an appropriate composite material and supports all or any part of a heart.

BRIEF DESCRIPTION OF THE DRAWINGS

FIG. 5 illustrates examples of values to input for the elastic moduli (the Young's modulus and Poisson ratio) as well as volume fraction of both connective tissue and cardiomyocyte.

FIG. 10 is a figure to depict an example of data to present the cardiomyocyte longitudinal orientations which the cardiac-structure-model construction part inputs.

FIG. 11 illustrates examples of geometry data for a cardiac structure model of an ellipsoid of revolution to represent the loft ventricular geometry at end systole.

FIG. 16 is a table to present an example of data which reflect the myocardial tissue characteristics distinctive among the three different hearts of control and concentric and eccentric hypertrophy and define structures and mechanical properties of a composite material in individual cardiac structure models for the three groups of heart.

FIG. 17 is a table to present an example of values for geometry data and values for pressure load which are individually defined in the cardiac structure models of a control heart and hearts of concentric and eccentric hypertrophy.

FIG. 22 B depicts only the inner layer 52a of the composite material sheet.

FIG. 23 A depicts an example of a laminate comprising three layers of composite material sheets. FIG. 23 B depicts only the middle layer, and FIG. 23C depicts only the inner.

FIG. 27 is a table to depict examples of orientations and volume fractions of reinforcement fiber which are determined in 3 cardiac structure models of composite material individually representing a normal heart, a diseased heart 1, and diseased heart 2.

DESCRIPTION OF THE PREFERRED EMBODIMENTS

The present embodiment is a simulation system of cardiac function wherein a cardiac structure model of the left ventricle is generated based on a composite material view of myocardial tissue which contains reinforcement fiber and matrix. The simulation system, using the cardiac structure model, predicts a change in left ventricular geometry by computation. The simulation system of cardiac function is able to predict a geometry change not only of the left ventricle but also of a whole heart or other cardiac chambers including the right atrium.

A Configuration of the Simulation System of Cardiac Function

Figure 1:
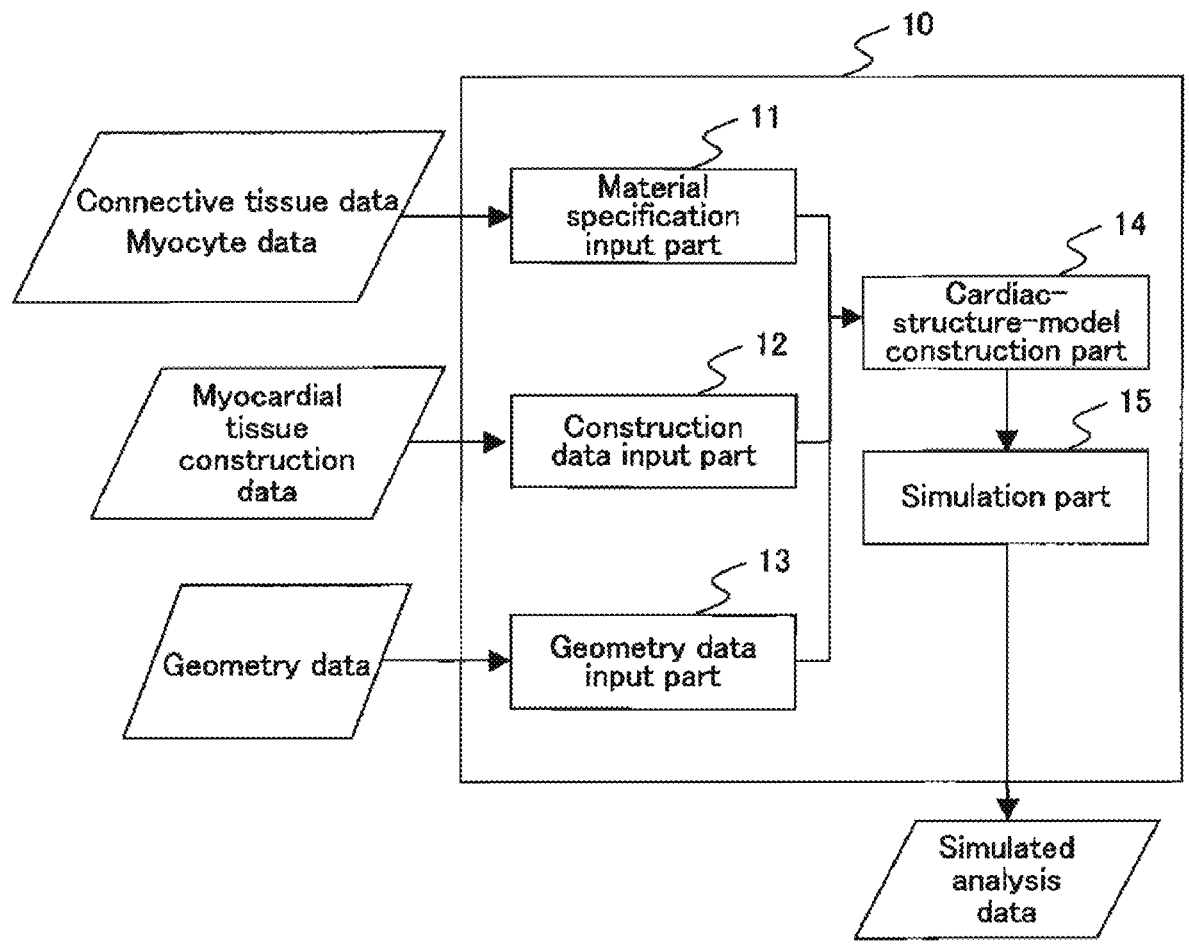
FIG. 1 is a function block diagram to indicate a configuration of a simulation system of cardiac function in the present embodiment.

FIG. 1 depicts a function block diagram to indicate a configuration of the simulation system of cardiac function in the present embodiment. As indicated in FIG. 1 a simulation system of cardiac function 10 in the present embodiment contains a material specification input part 11, a construction data input part 12, a geometry data input part 13, a cardiac-structure-model construction part 14, and a simulation part 15.

The simulation system of cardiac function 10 is able to be built in a general-purpose instrument (noted as PC etc.) such as a personal computer or a work station. Functions of individual parts, a material specification input part 11, a construction data input part 12, a geometry data input part 13, a cardiac-structure-model construction part 14, and a simulation part 15, are proceeded by a CPU of PC etc. executing defined programs which are recorded on recording media equipped to the PC etc.

The present embodiment includes the programs which a PC etc. executes to develop processes of individual parts, the material specification input part 11, the construction data input part 12, the geometry data input part 13, the cardiac-structure-model construction part 14, and the simulation part 15. The present embodiment also includes the computer media which record the programs. A configuration of hardware is not necessarily the one indicated in FIG. 1. For example, functions of a simulation system of cardiac function 10 may be separated into more than one PC etc. which are connected through a computer network, LAN, etc. and share telecommunication.

The material specification input part 11 inputs both connective tissue data which present mechanical properties of connective tissue and myocyte data which present mechanical properties of cardiomyocyte within the myocardial tissue of a heart subject to the simulation. The mechanical properties include elastic modulus and strength. Mechanical properties of connective tissue and cardiomyocyte inputted in this part are preferably the values which are obtained experimentally or logically. Details of the mechanical properties of cardiomyocyte and connective tissue are described later.

The cardiac-structure-model construction part 12 inputs myocardial tissue construction data which represent the myocardial tissue architecture. The myocardial tissue construction data include, for example, the data for a volume fraction occupied by connective tissue within the myocardial tissue (noted below as a volume fraction of connective tissue), the data for cell diameter of cardiomyocyte, and the data to present longitudinal orientations of cardiomyocyte or connective tissue.

The geometry data input part 13 inputs geometry data of three-dimensional geometry of the heart subject to the simulation. The geometry data are not necessarily three-dimensional geometry of a whole heart, but can be the data sufficient enough to represent a part of heart which needs a simulation. The geometry data may be the data based on a measured geometry of an actual heart, or the data of geometrical shape imitating a shape of a heart. For example, geometrical shapes imitating a shape of the left ventricle include thick-wall ellipsoid of revolution and thick-wall truncated ellipsoid of revolution.

The data inputted in the material specification input part 11, the construction data input part 12, and the geometry data input part 13 are recorded in a recording part (recording media such as memory: not depicted in the figure) contained by the simulation system of cardiac function 10, and are readily available by the cardiac-structure-model construction part 14. The material specification input part 11, the construction data input part 12, and the geometry data input part 13 may input new data by reading files which contain the data to input. The three parts 11, 12, and 13 may also be compatible with a process of data inputted by a user through different input tools (not depicted in the figure) equipped to the PC etc. such as a keyboard and a mouse.

The cardiac-structure-model construction part 14, utilizing the geometry data inputted in the geometry data input part 13, generates the cardiac structure model which assumes assembly of finite elements and represents a heart subject to a simulation. The cardiac-structure-model construction part 14, utilizing myocardial tissue construction data inputted in the construction data input part 12, generates the cardiac structure model which assumes the ventricular wall of heart made of a composite material containing reinforcement fiber and matrix. The cardiac-structure-model construction part 14 also defines mechanical properties of the reinforcement fiber with those of the connective tissue data inputted in the material specification input part 11 and defines mechanical properties of matrix with those of myocyte data inputted in the material specification input part 11.

The simulation part 15, utilizing finite element method, proceeds the computation processing and simulates a change of geometry of a cardiac structure model under pressure load to the heart which the model represents. The function of a simulation part 15 is executed using a general FEM (finite element method)-Software on the market. The simulation part 15 thus outputs simulated analysis data and records them. The simulated analysis data are presented, printed, or used by another computation system. The simulation part 15 outputs the simulated analysis data including a change in volume and shape of the heart subjected to the simulation as well as data indicating characteristics of torsion of the myocardium.

An Example of Execution of a Cardiac Function Simulation System

Figure 2:
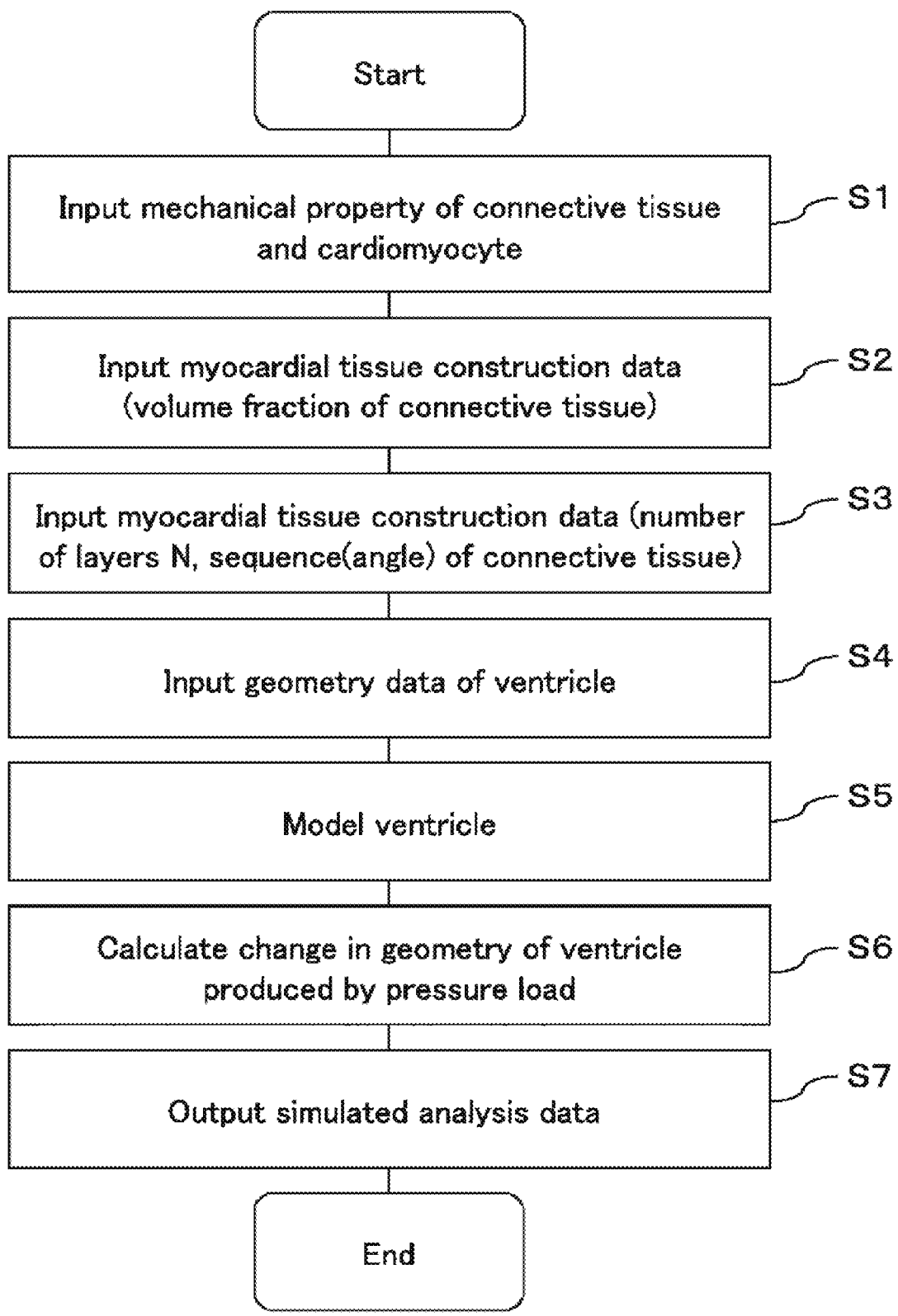
FIG. 2 is a flow chart to indicate steps in the execution of the cardiac function simulation system.

The following is a description for example of execution of the cardiac function simulation system 10 in the present embodiment. FIG. 2 depicts a flow chart to indicate steps in the execution of cardiac function simulation system. Here provided is an explanation in a case of simulation of geometry change of the left ventricle of a human heart.

First, the material specification input part 11 inputs connective tissue data and myocyte data (Step S1). In the present embodiment the material specification input part 11 inputs, for example, the Young's modulus and Poisson' ratio of connective tissue as the connective tissue data, and the Young's modulus and Poisson' ratio of cardiomyocyte as the myocyte data. The material specification input part 11, may also input the shear stiffness of cardiomyocyte as the myocyte data.

Figure 3A:
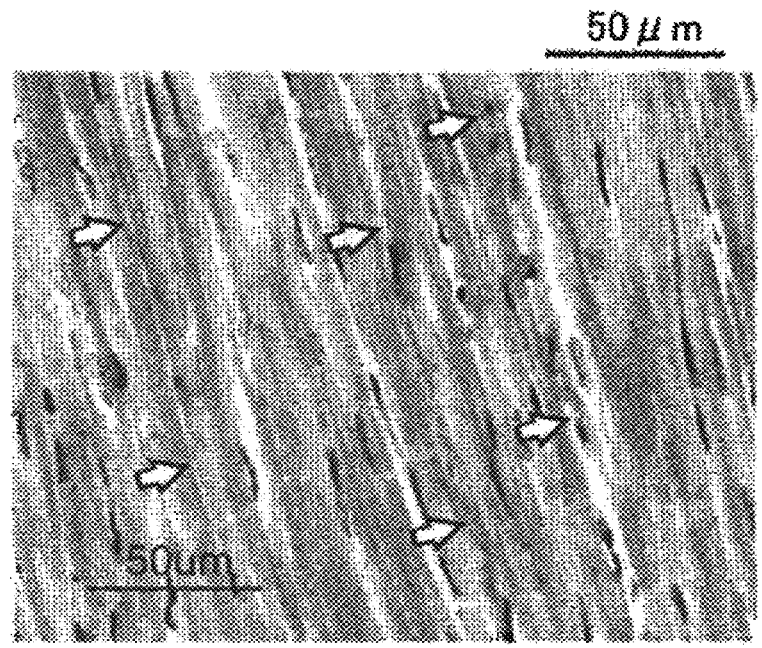
FIG. 3A is a light micrograph to depict the myocardial tissue exhibiting longitudinal profiles of cardiomyocyte.
Figure 3B:
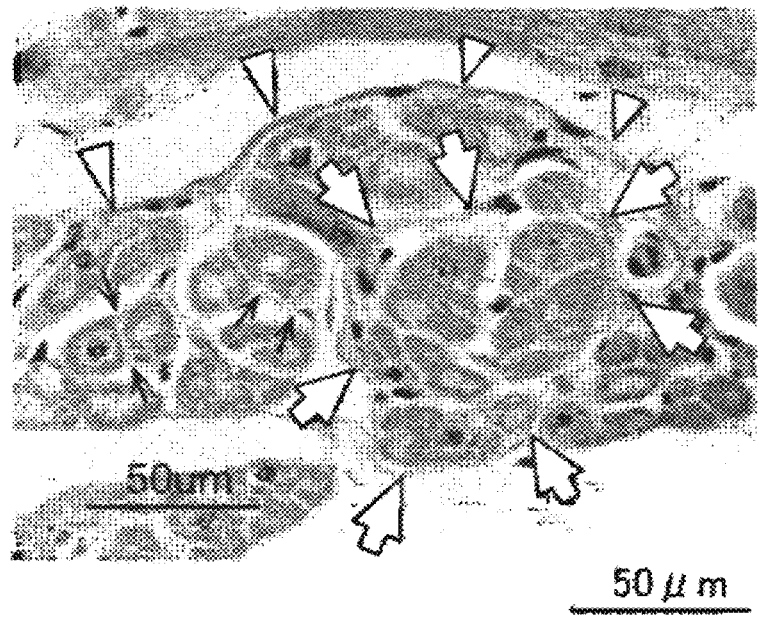
FIG. 3B is a light micrograph to depict the myocardial tissue containing cardiomyocytes with cross sectional profiles.

It is a common observation that the myocardial tissue contains both numerous cardiomyocytes which often connect each other along their longitudinal orientations and connective tissues which occupy the interstitial spaces among the cardiomyocytes. FIG. 3A is a light micrograph to depict the myocardial tissue presenting longitudinal profiles of cardiomyocyte. FIG. 3B is a light micrograph to depict the myocardial tissue containing cardiomyocytes with cross sectional profiles. Different types of arrows in FIGS. 3A and 3B all indicate various connective tissues within the myocardial tissue. The connective tissue is mainly composed of collagen fiber. Collagen fiber is stiffer than cardiomyocyte. For instance, based on comparative examinations of the elastic properties of connective tissue and cardiomyocyte by experimental and theoretical studies, the assumption value for the Young's modulus of connective tissue is around 100 MPa or more, and the assumption value for the Young's modulus of cardiomyocyte is around 200 KPa or less. This indicates that a value for the Young' modulus of connective tissue is as large as one hundred times or more of a value for the Young' modulus of cardiomyocyte.

Accordingly, values for the Young's modulus of connective tissue, preferably as large as one hundred times or more of values for the Young's modulus of cardiomyocyte, are inputted by the material specification input part 11 in Step S1. For example, when a user determines values which the material specification input part 11 inputs, a predetermined range of comparative values for the Young's modulus, consistent with a difference preferably defined above, may be provided. The Young's modulus and Poisson' ratio of connective tissue are used as values for material specification of reinforcement fiber within a composite material which composes the cardiac structure model generated in the cardiac-structure-model construction part 14. By defining values for the Young's modulus of the connective tissue as large as one hundred times or more of values for the Young's modulus of the cardiomyocyte, values for the Young's modulus of reinforcement fiber are accordingly determined as large as one hundred times or more of values for the Young's modulus of matrix within the composite material. Thus it is possible to obtain a cardiac structure model comprising the composite material which possesses the material characteristics of FRR, as would be described below.

Figure 4:
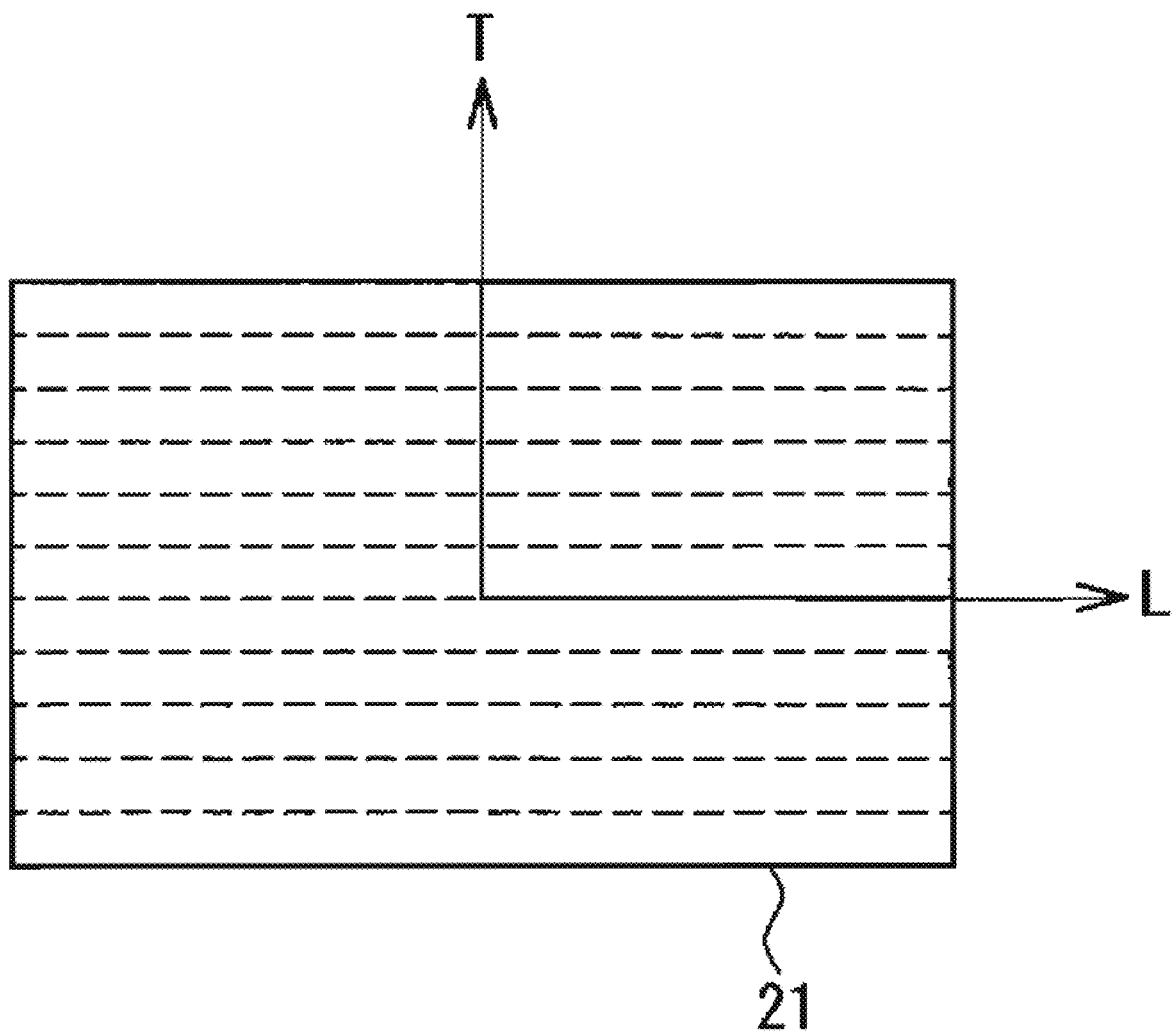
FIG. 4 is a surface view of a plate made of unidirectional fiber reinforced rubber.

Here provided is a theoretical implication for a difference as large as one hundred times in value for the Young's modulus between reinforcement fiber and matrix. FIG. 4 depicts a surface view of a plate 21 made of unidirectional fiber reinforced rubber. Dotted lines in the figure indicate orientations of unidirectional reinforcement fibers. A long arrow L indicates an axis parallel to a longitudinal orientation of the unidirectional reinforcement fibers, and a long arrow T indicates an axis perpendicular to the longitudinal orientation of fibers. The elastic moduli of the plate 21 are given by the following formulas (Math 1)-(Math 5) according to a composite theory. In these formula affiliation letters L and T indicate axes L and T in FIG. 4, and affiliation letters m and f indicate matrix and reinforcement fiber. Thus $E_L$ and $E_T$ individually mean the Young's moduli of the plate along axes L and T, $v_L$ and $v_T$ individually mean the Poisson' ratios of the plate along axes L and T, and $G_{LT}$ means shear stiffness of the plate. In the formulas (Math 1)-(Math 5), $E_L$, $E_T$, $v_L$, $v_T$, and $G_{LT}$, independent each other, individually imply different elastic moduli of the plate. $E_m$ and $E_f$ individually mean the Young's modulus of matrix and reinforcement fiber, and $V_m$ and $V_f$ individually mean the volume fractions of matrix and reinforcement fiber.

$$E_L = E_f V_f + E_m V_m \quad \text{(Math 1)}$$

$$\frac{1}{E_T} = \frac{V_f}{E_f} + \frac{V_m}{E_m} - V_f V_m \frac{\left(\frac{v_m}{E_m} - \frac{v_f}{E_f}\right)^2}{\frac{V_f}{E_m} + \frac{V_m}{E_f}} \quad \text{(Math 2)}$$

$$v_L = v_f V_f + v_m V_m \quad \text{(Math 3)}$$

$$v_T = v_L \frac{E_T}{E_L} \quad \text{(Math 4)}$$

$$\frac{1}{G_{LT}} = \frac{V_f}{G_f} + \frac{V_m}{G_m} \quad \text{(Math 5)}$$

The Maxwell-Betti's reciprocal theorem depicted in (Math 6) is applied in each of the formulas (Math 1)-(Math 5).

$$\frac{E_L}{E_T} = \frac{v_L}{v_T} \quad \text{(Math 6)}$$

Given the values for the Young's modulus of reinforcement fiber as large as one hundred times or more of those of rubber as matrix, and given the incompressibility of rubber, assumptions indicated by the following formulas (Math 7) and (Math 8) are applied here.

$$E_f \gg E_m \quad \text{(Math 7)}$$

$$v_m = \frac{1}{2} \quad \text{(Math 8)}$$

Formulas (Math 7) and (Math 8) are given to Formulas (Math 1)-(Math 5), and the following approximations (Math 9)-(Math 12) are provided.

$$E_L \approx E_f \cdot V_f \gg E_T \quad \text{(Math 9)}$$

$$E_T \approx \frac{E_m}{V_m} \frac{1}{(1-v_m^2)} \approx \frac{4}{3} \frac{E_m}{V_m} \quad \text{(Math 10)}$$

$$v_T \approx 0 \quad \text{(Math 11)}$$

$$G_{LT} = \frac{G_m}{V_m} \quad \text{(Math 12)}$$

Given further examination of shear strength of the plate, it is proved experimentally as well as theoretically that an approximation formula (Math 13) to give $G_{LT}$, depicted below, is applicable for any value for the volume fraction of reinforcement fiber.

$$G_{LT} = \frac{E_T}{4} \quad \text{(Math 13)}$$

Approximations for the elastic moduli of plate s given by the formulas (Math 9)-(Math 13) are unique to FRR, which possesses values for the Young's modulus of reinforcement fiber as large as one hundred times or more of values for the Young's modulus of matrix. Thus a difference as large as one hundred times in value for the Young's modulus between reinforcement fiber and matrix in FRR implies that values for the Young's modulus of reinforcement fiber is large enough compared to that of matrix so that the approximation formulas (Math 9)-(Math 13) are practically applicable.

In the next step, the cardiac-structure-model construction part 12 inputs values for a volume fraction of connective tissue as myocardial tissue construction data (Step S2). The cardiac-structure-model construction part 12 may be used to input the data presenting a volume fraction of connective tissue which are provided by a user. For example a user, when simulating a cardiac function of a control heart, is able to use the cardiac-structure-model construction part 12 to input a mean value of a volume fraction of connective tissue which is commonly known for human control hearts. FIG. 5 depicts examples of values for the elastic moduli (the Young's modulus and Poisson' ratio) as well as volume fraction of both connective tissue and cardiomyocyte which the cardiac-structure-model construction part 12 may input. The values depicted in the figure are examples based on previous findings of different hearts. The cardiac-structure-model construction part 12 may also input different data, other than values for volume fraction, such as those for a cell diameter of cardiomyocyte.

The cardiac-structure-model construction part 12 also inputs, as the myocardial tissue construction data, the number of layers of laminate which composes a ventricular wall of heart as well as data to represent longitudinal orientations of cardiomyocyte (Step S3). As described below, the cardiac-structure-model construction part 14 is able to provide a cardiac structure model of the left ventricle wherein the ventricular wall comprises multiple layers of curved sheets of composite material. The number of layers in the laminate, N, in the cardiac structure model is used as the number of layers of curved sheet laminate in this step. Data for orientations of cardiomyocyte within the myocardial tissue are used to determine orientations of reinforcement fiber within individual curved sheets of the laminate in this step.

Figure 6A:
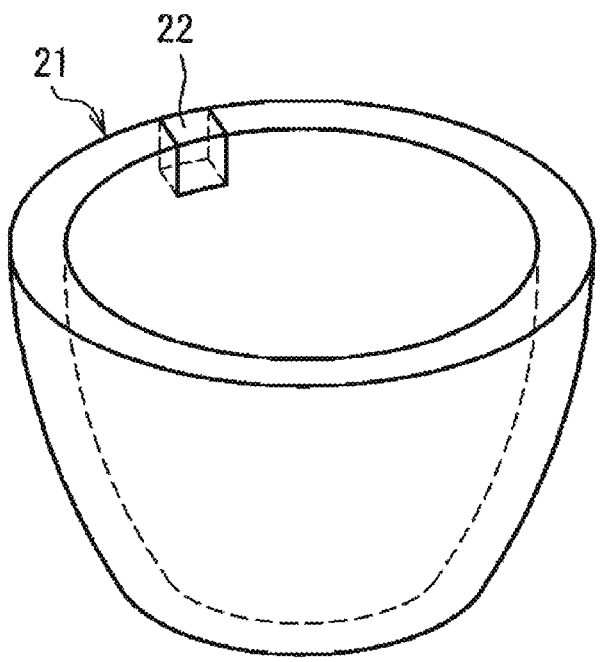
FIG. 6A is an illustration to depict the left ventricle.
Figure 6B:
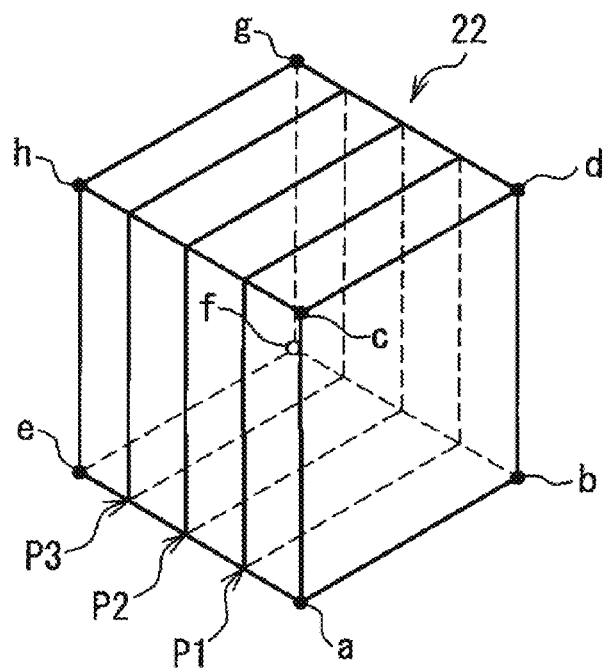
FIG. 6B is an enlarged figure of a cubic tissue which is separated from the left ventricular wall depicted in FIG. 6A.

Here provided is a description for a change in orientation of longitudinal alignment of cardiomyocyte within the myocardial tissue layers of ventral wall. FIG. 6A is an illustration to depict the left ventricle. FIG. 6B is an enlarged figure of a cubic tissue part 22 which is separated from the left ventricular wall depicted in FIG. 6A. In the tissue part 22 depicted in FIG. 6B, a cubic face a-b-c-d represents the endocardium of left ventricle and a cubic face e-f-g-h represents the ventricular epicardium.

Figure 7A:
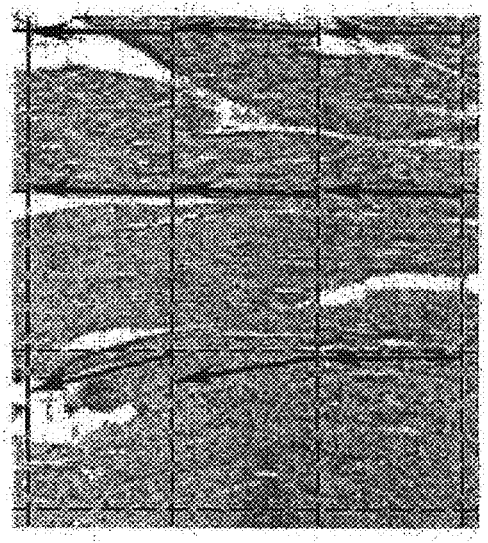
FIGS. 7A to 7C are light micrographs to exhibit myocardial tissues on tangential sections P1, P2, and P3 which are indicated in FIG. 6B.
Figure 7B:
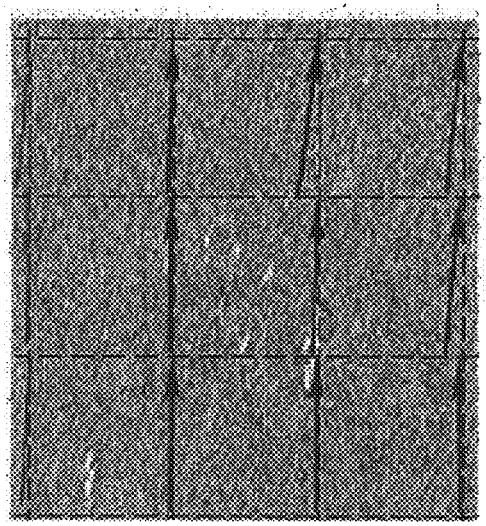
Figure 7C:
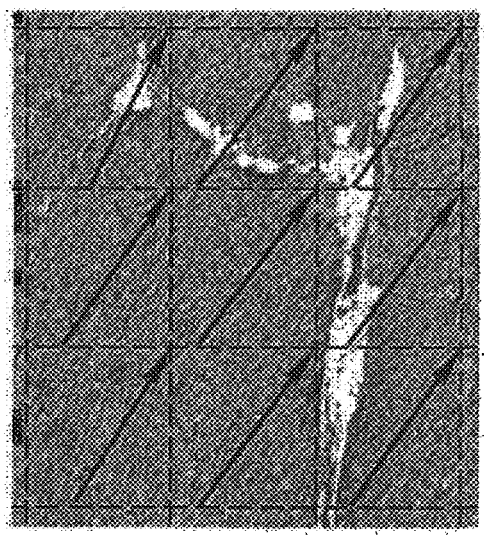

When three cross sections P1, P2, and P3, each perpendicular to the transmural axis (along an edge a-e) of tissue part 22, are exposed and observed from the endocardial side of the ventricle, tissues on the individual sections represent light micrographic images such as those depicted in FIGS. 7A-7C. A grid (0.3 mm edge) is superimposed on each micrograph, and orientations of cardiomyocyte longitudinal alignment determined at individual square grids are indicated by arrows in the figures. As depicted in the three figures, the orientations of cardiomyocyte longitudinal alignment, when observed on tangential planes within the ventricular wall, changes in directions along different transmural positions. It is a common observation that the orientations of cardiomyocytes continuously changes in direction along different through-wall positions from the endocardium to epicardium, as illustrated in the figures.

Figure 8:
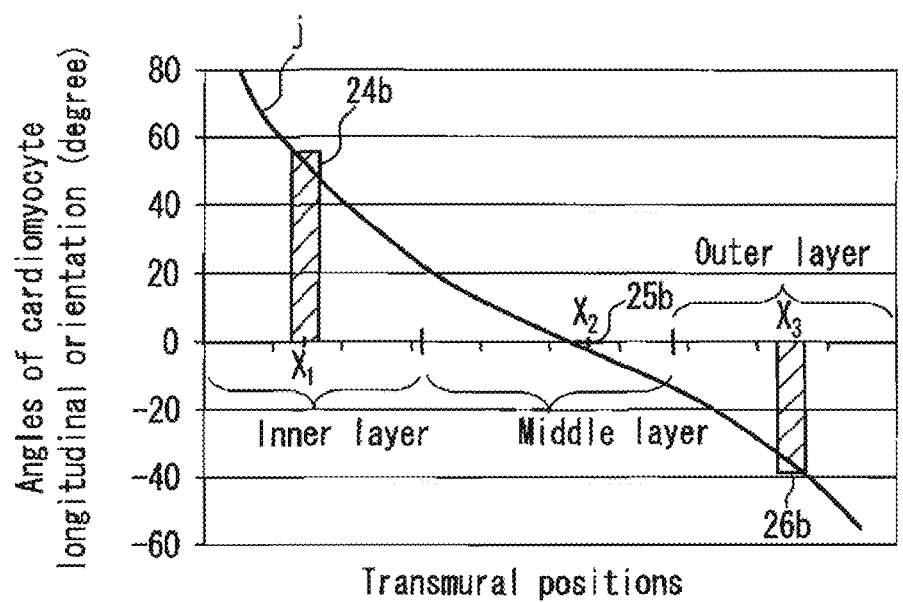
FIG. 8 is a graph to represent a transmural change of cardiomyocyte longitudinal orientation within the ventricular wall.

FIG. 8 depicts a graph to represent a transmural change of cardiomyocyte longitudinal orientation within the ventricular wall. A horizontal axis indicates different transmural positions within the ventricular wall and a vertical axis indicates angles of cardiomyocyte longitudinal orientation relative to a geometric reference plane. A plane perpendicular to a large axis of a geometry model of ellipsoid of revolution for the ventricle (a short axis plane of the ellipsoid of revolution) may be assigned as a reference plane. A curve j in the graph presents longitudinal orientations (mean values) of cardiomyocytes at different transmural positions of the left ventricular wall in control human hearts. A shape of the curve may differ in diseased human hearts.

Figure 9:
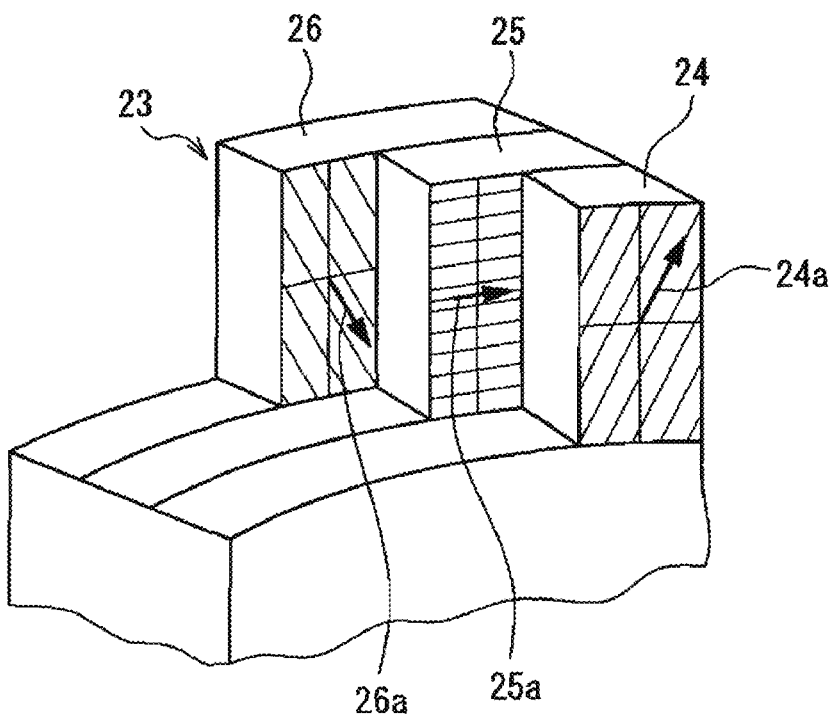
FIG. 9 is an illustration of a concept of 3-layers model for the left ventricular wall.

Among different modeling to represent the ventricle which possesses characteristic changes in longitudinal orientation of cardiomyocyte along the transmural direction such as those described above, there is an approach to assume an N-layers model for the ventricular wall which contains N-layers of curved sheets of composite material laminated along the transmural direction. FIG. 9 illustrates a concept of an N-layers model in which N equals 3. The model in the figure represents a 3-layers model for the ventricular wall 23 which comprises 3 curved sheets, the inner layer 24, middle layer 25, and outer layer 26, made of composite material containing reinforcement fibers. Orientation of the reinforcement fibers within individual layers, indicated as arrows 24a, 25a, and 26a in the figure, changes stepwise.

In an N-layers model of the ventricular wall, it is preferable that orientations of reinforcement fiber within individual model layers reflect the orientations of cardiomyocyte longitudinal alignment within different tissue layers of the ventricular wall which individual model layers represent. The cardiomyocyte longitudinal orientations within different tissue layers of the ventricular wall, mentioned above, may be defined by representative angle values (such as mean values) of the orientations of cardiomyocyte longitudinal alignment relative to a particular reference plane.

Three bars 24b, 25b, and 26b, depicted within a graph of FIG. 8, individually present a representative value for the cardiomyocyte longitudinal orientation of inner, middle, and outer layer of the ventricular wall, respectively. A representative value for the cardiomyocyte longitudinal orientation in the inner layer, middle layer or outer layer, 24, 25, or 26, may be individually defined by a values of the curves at the position x1 (a value indicated by a bar 24b), x2 (a bar 25b), and x8 (a bar 26b), respectively. Thus digitalized data at the inner, middle, and outer layers, representing a particular change in longitudinal orientation of cardiomyocytes presented by a curve j at different transmural positions of the left ventricular wall, are inputted in the cardiac-structure-model construction part 12 as data to determine the orientations of cardiomyocyte longitudinal alignment. Thus, by inputting the data to present cardiomyocyte longitudinal orientations which sequentially change along the inner, middle, and outer layers of the ventricular wall, a particular change in longitudinal orientation of cardiomyocytes presented by a curve j at different transmural positions of the left ventricular wall of control human hearts can be reflected in the cardiac structure model, as is described below.

FIG. 10 depicts an example of data to present the cardiomyocyte longitudinal orientations which the cardiac-structure-model construction part 12 inputs. In this example depicted in FIG. 10, the cardiomyocyte orientations are defined for 3 layers of the inner, middle, and outer layers of the left ventricle, and are presented as angle values relative to a reference plane that is parallel to a short axis of a geometry model of ellipsoid of revolution for the ventricle. A value is positive when an angle is of a counter-clock wise direction relative to the reference as viewed from the endocardial side of the ventricular wall.

The data depicted in FIG. 10 present twelve different patterns of sequence in cardiomyocyte longitudinal orientation along the inner, middle, and outer layers; type 1 to type 12. In each type of sequence, angles for the inner, middle, and outer layers are +θ degrees, 0 degree, and −θ degrees, respectively. That is, the angle for middle layer is 0 degree, and the angles for inner and outer layers are of the same value but of reverse directions, positive and negative. A model with an odd number of layers (for example, 3-layers model) and an assignment of 0 degree angle for the cardiomyocyte longitudinal orientation in the mid-layer of laminate (the middle layer in 3-layers model) is based on the following observation of the left ventricular wall in actual hearts. In the actual hearts the circular muscle exists at the mid-wall of the ventricle, that is, a transmural position consistent with the mid-layer in the laminate model. The longitudinal orientations of cardiomyocyte within the circular muscle are predominantly 0 degree. Thus the cardiac structure model with the assumption of ventricular wall of an odd number of layers well reflects the cardiomyocyte longitudinal orientations within the circular muscle found in an actual left ventricular wall.

Among the twelve different patterns, type 1 to type 12, of sequence in cardiomyocyte longitudinal orientation along the inner, middle, and outer layers, cardiomyocyte longitudinal orientations in all three of the inner, middle, and outer layers are along the circumferential direction of the ventricle, that is, parallel to a short axis plane of the ellipsoid of revolution, in type 1. In type 8 angles for reinforcement fibers within the inner and outer layers both possess a value of complement (35.3 degrees) of a specific bias angle (54.7 degrees), but of reversed directions. In this type, by utilizing a value of a specific bias angle for the data to represent cardiomyocyte longitudinal orientations in a cardiac structure model, an implication of a specific bias angle within the myocardial architecture can be analyzed in reference to a cardiac function, which has never been examined. In type 12, angles for reinforcement fibers within the inner, middle and outer layers separate half a circle (180 degrees) at equal intervals. That is, the type 12 represents a pattern of sequence in angles for reinforcement fibers with equal intervals from +90 degrees to −90 degrees. This pattern of angle sequence is equivalent to an angle sequence in a laminate which is composed of numerous laminas with fiber angles continuously changing from +90 degrees to −90 degrees. The data depicted in FIG. 10 present only examples for different patterns of sequence in cardiomyocyte longitudinal orientation along the inner, middle, and outer layers, and the patterns are not always limited to the cases in the figure.

Values for cardiomyocyte longitudinal orientation, a volume fraction of connective tissue, a diameter of cardiomyocyte, and others which the cardiac-structure-model construction part 12 inputs in Step S2 and Step S3 are based on different data including, but not limited to, those obtained by microscopic observation. The cardiac-structure-model construction part 12 may input, for example, values for cardiomyocyte longitudinal orientation, a volume fraction of connective tissue, a diameter of cardiomyocyte, and others which are based on clinical data obtained by measurement instruments such as x-ray diagnostic instruments, ultrasound diagnostic instruments, and MRI.

The geometry data input part 13 inputs geometry data to represent three-dimensional geometry of the left ventricle (Step S4). For example, The geometry data input part 13 inputs geometry data to represent a thick-wall, truncated ellipsoid of revolution (an ellipsoid of revolution separated at a short axis plane). In this case values such as major and miner radii of ellipse as well as wall thickness are inputted as the geometry data. These values may be determined, for example, based on geometric characteristics of the end-systolic loft ventricle in control human hearts. FIG. 11 provides examples of geometry data inputted for a cardiac structure model of ellipsoid of revolution to represent the left ventricular geometry at end systole.

In the present embodiment an explanation is provide for a case wherein the cardiac function simulation system 10 simulates a geometry change of the end-systolic left ventricle which is produced by pressure load into the cavity. However examples for the simulation which the simulations system can precede are not limited to the case provide here. For instance the simulation system can simulate a geometry change in a cardiac structure model for the end-diastolic left ventricle which is produce by negative pressure of suction into the cavity.

The geometry data which the geometry data input part 13 inputs are not limited to those representing conventional geometric contours such as the ellipsoid of revolution described above. For example the geometry data input part may input, as the geometry data, different data of a cardiac shape which are clinically observed by measurement instruments such as x-ray diagnostic instruments, ultrasound diagnostic instruments, and MRI.

The cardiac-structure-model construction part 14 generates a cardiac structure model which assumes assembly of finite elements and represents myocardial tissue of the ventricular wall based on the data inputted through Step S1 to S4. (Step S5). In the cardiac-structure-model construction part 14, a number of finite elements compose the three-dimensional geometry of the left ventricle represented by the geometry data which the geometry data input part 13 inputs. Nodes are assigned in individual finite elements. In each finite element values are determined for mechanical properties which are defined by connective tissue data and myocyte data the material specification input part 11 inputs. In this process, according to the construction data presented by the myocardial tissue construction data which the cardiac-structure-model construction part 12 inputs, various values to characterize mechanical properties are determined for individual finite elements.

Among practical examples of values for mechanical properties of finite elements, the cardiac-structure-model construction part 14 defines a finite element stiffness matrix for each finite element by utilizing data such as geometry data, myocardial tissue construction data, mechanical properties of connective tissue, and mechanical properties of cardiomyocytes. The cardiac-structure-model construction part 14 then defines a global stiffness matrix based on the finite element stiffness matrices.

Figure 12:
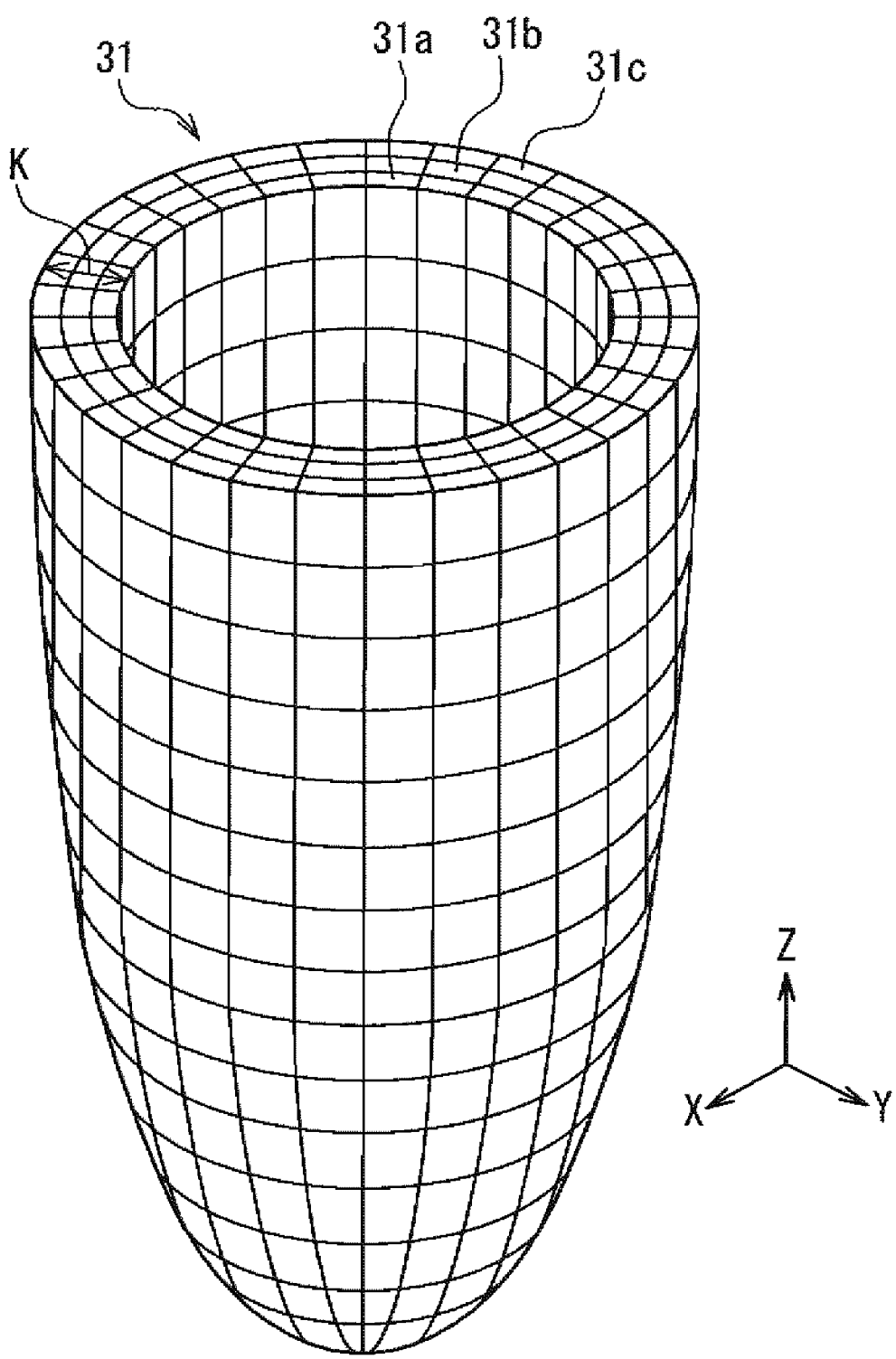
FIG. 12 is a figure to present an example of the cardiac structure model of an ellipsoid of revolution defined by geometry data which is composed of a number of finite elements.

Here provided is a description for a case wherein the cardiac-structure-model construction part 14 provides a cardiac structure model of an ellipsoid of revolution to represent the left ventricle with a wall comprising 3 layers of curved sheets of composite material. FIG. 12 depicts an example of a cardiac structure model of an ellipsoid of revolution defined by geometry data which is composed of a number of finite elements. A cardiac structure model 31 depicted in FIG. 12 is an ellipsoid of revolution characterized by an ellipse possessing z-axis as a large axis and x or y axis as a short axis as well as a constant wall thickness of k. In a cardiac structure model 31, the ventricular wall is separated into 3 tangential layers, and each layer comprises a number of finite elements. Thus the ventricular wall in the cardiac structure model 31 is defined as an assembly of finite elements possessing 3 layers architectures. That is, a group of finite elements composing the endocardial one-third of ventricular wall, the inner layer 31a (noted as the inner layer group of elements below), a group of finite elements composing the mid-layer of ventricular wall, the middle layer 31b (noted as the middle layer group of elements below), and a group of finite elements composing the epicardial one-third of ventricular wall, the outer layer 31c (noted as the outer layer group of elements below), the three groups of finite elements all together compose the cardiac structure model 31 of an ellipsoid of revolution.

Assembly of finite elements is not limited to a pattern indicated in an example of cardiac structure model of FIG. 12. For instance, the number of layers composing the ventricular wall is not limited to three. Sizes of individual finite elements are not always same. A part of the cardiac structure model which requires detailed analysis may be separated into finite elements of smaller sizes.

Figure 13:
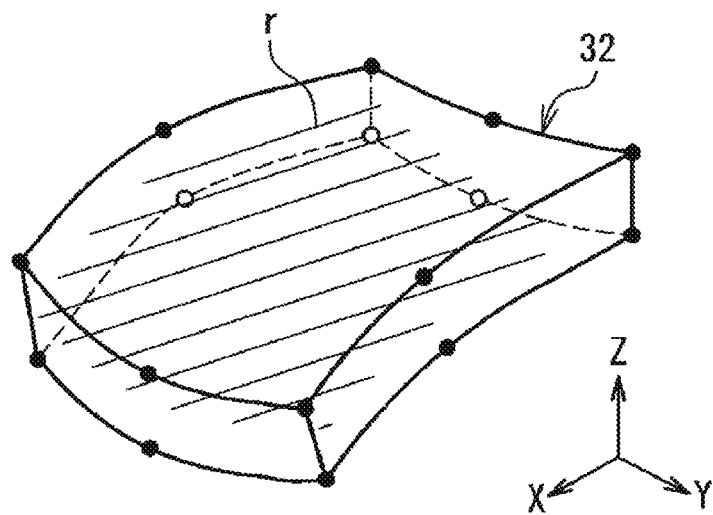
FIG. 13 is a figure to present the cardiac structure model made of a composite material possessing reinforcement fibers embedded within matrix which is modeled as a continuum element.

The cardiac-structure-model construction part 14 defines material specifications of a composite material comprising reinforcement fiber and matrix for individual finite elements. For example, the cardiac-structure-model construction part 14 may define particular composite characteristics for finites elements which reflect mechanical properties and longitudinal orientations of reinforcement fiber as well as mechanical properties of matrix. That is, the cardiac-structure-model construction part 14 is able to provide a cardiac structure model containing a laminate of macro anisotropic material, a material model which represents a uniform material combining reinforcement fiber and matrix together. Utilizing such cardiac-structure-model of macro anisotropic material, a cardiac structure model which contains the ventricular wall possessing mechanical characteristic of unidirectional fiber-reinforced composite material is provided. As a practical example for such macro anisotropic material, the cardiac-structure-model construction part 14 may provide a cardiac structure model made of a composite material possessing reinforcement fibers embedded within matrix which is modeled as a continuum element. In the example indicated in FIG. 13, reinforcement fiber element r, named as Rebar element, is embedded within matrix utilizing an isoparametric coordinate of matrix element (mechanical properties for reinforcement fiber and those for matrix are integrated into those of a macro-material), and a model of composite material with particular mechanics, model 32, is provided.

A composite material composing a cardiac structure model is not limited to a laminate of macro anisotropic material possessing mechanical properties which are characterized by those of reinforcement fiber and matrix, not individually but all together. Another example of composite material model includes an architecture comprising distinct elements of reinforcement fiber and matrix. In this case of composite material model architectural characteristics of reinforcement fibers such as diameter, center-to-center distance, shape, and distribution pattern of fibers are individually defined. Interface mechanics between reinforcement fiber and matrix is also specifically defined and taken into consideration in the simulation of cardiac function. For example, in order to analyze how the myocardial tissue characteristics such as a cell diameter and a center-to-center distance of cardiomyocyte, in addition to a volume fraction of connective tissue, may possibly participate in a cardiac function, the simulation of cardiac function needs to proceed using a cardiac structure model in which a diameter and a center-to-center distance of reinforcement fiber reflects the tissue characteristics mentioned above. The cardiac structure model with a particular composite material comprising distinct elements of reinforcement fiber and matrix may facilitate such simulation of cardiac function which reflects the myocardial tissue characterization.

In this cardiac structure model comprising distinct elements of reinforcement fiber and matrix, mechanical properties of reinforcement fiber are defined according to the Young's modulus and the Poisson' ratio of connective tissues which a material specification input part 11 inputs, and mechanical properties of matrix are defined according to the Young's modulus and the Poisson' ratio of cardiomyocyte which a material specification input part 11 inputs. By defining values for the Young's modulus of reinforcement fiber as large as one hundred times or more of values for the Young's modulus of matrix in the composite model, a cardiac structure model which contains the ventricular wall made of laminate of thin FRR sheets tangent to local ventricular surfaces is developed. Fiber reinforced rubbers possess unique mechanical properties which other types of fiber reinforced composite materials, such as fiber reinforced plastics (FRP), do not. For example there exists a 'specific bias angle in FRR composites.

The myocardial tissue structures within the ventricular wall of an actual heart are considered to present a composite architecture which possesses the unique mechanical properties attributed to 'specific bias angle.' Given the rubber composite characteristics of the actual myocardial tissue, a cardiac structure model containing the ventricular wall made of FRR composites may better facilitate a simulation of cardiac function. Such simulation benefits a clarification of cardiac pathophysiology, which the conventional approaches have failed.

In this cardiac structure model comprising distinct elements of reinforcement fiber and matrix, longitudinal orientations of reinforcement fiber are defined according to the data representing longitudinal orientations of cardiomyocyte which the cardiac-structure-model construction part 12 inputs. For example, in the simulation of cardiac function wherein different values individually representing cardiomyocyte longitudinal orientations within the inner, middle, and outer layer are inputted in Step S3, the input values for individual layers are used to determine longitudinal orientations of reinforcement fiber for the particular finite element groups within the inner, middle, and outer layers.

Values for a volume fraction of connective tissue which the cardiac-structure-model construction part 12 inputs also provide the information in defining a diameter of connective tissue. With an assumption that cardiomyocytes and distributions of connective tissue surrounding the cardiomyocytes are in one-to-one relation in prevalence, a calculation utilizing both values for a volume fraction of connective tissue and values for a diameter of cardiomyocyte may provide values for a diameter of reinforcement fiber in the cardiac structure model. In a case of the simulation of cardiac function wherein the cardiac-structure-model construction part 12 inputs values for a diameter of cardiomyocyte, values for a center-to-center distance of reinforcement fibers may be determined based on the values for a cardiomyocyte diameter. Methods or calculations to obtain values for a diameter and a center-to-center distance of reinforcement fiber in the cardiac-structure-model include the ones described above but not limited to them.

Figure 14:
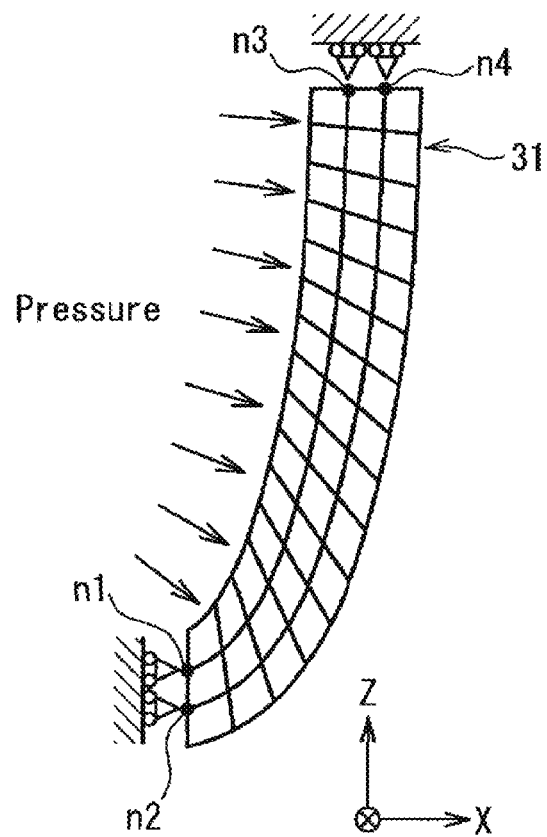
FIG. 14 is an illustration to depict an example of the boundary conditions and pressure load in a simulation.

Utilizing the cardiac-structure-model of the left ventricle generated as above, the simulation part 15 determines boundary conditions in finite element method, and proceeds a computation processing to simulate a change of geometry of the left ventricle which is produced by pressure load to the cavity (Step S6). FIG. 14 depicts an illustration to depict an example of the boundary conditions and pressure load in a simulation. The figure illustrates the x-z plane, particularly of the right half of the z axis, in the cardiac structure model 31 depicted in FIG. 12. The boundary conditions indicated in FIG. 14 are characterized by two restrictions. One is a restriction, applied for nodes n1 and n2 on z-axis defined on an element of the ventricular middle layer at the apex, that a shift would be allowed only along z axis, but not along either x or y axis. The other one is a restriction, applied for nodes n3 and n4 defined on an element of the ventricular middle layer at the base, that a shift would be allowed only along either x or y axis, but not along z axis. A pressure load is applied along a direction indicated by arrows in the figure. Values for the pressure load vary, and may be 20 KPa, for example. The pressure values may reflect the left ventricular pressure in a physiologic condition of cardiac cycle of human hearts. In an example indicated in FIG. 14 a positive pressure is applied so that the ventricular cavity would be extended. In another example, however, a pressure may also be negative so that the cavity would reduce its size.

The simulation part 15, following a computation processing and simulation of a change of geometry of a cardiac structure model, outputs simulated analysis data (Step S7). The simulated analysis data include a change in volume and shape of the ventricle accompanying a change in the cavity pressure as well as data indicating torsion of the ventricular wall. A process of the output is not limited to the one described above but may optionally vary to fit any purpose. For example, the simulation part 15 may output data such as a motion picture to depict a change in shape of the ventricular cavity and wall.

Examples of a Use of Simulation Analysis Data

Figure 15:
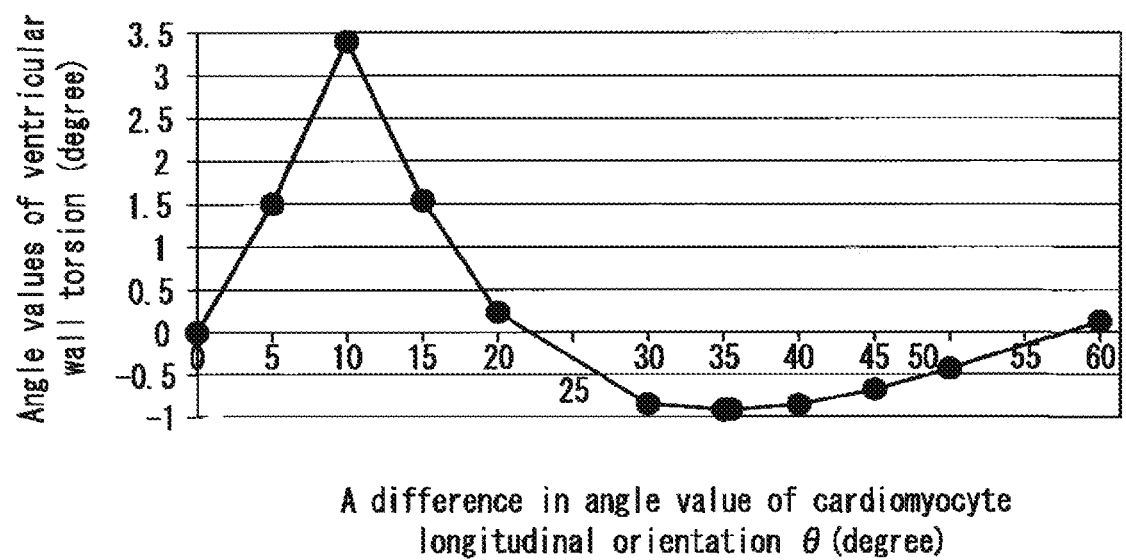
FIG. 15 is a graph presenting an example of analysis data of simulation by the simulation part 15.

FIG. 15 depicts a graph presenting an example of analysis data of simulation by a simulation part 15. The graph in this figure depicts torsion of the ventricular wall simulated for individual cardiac structure models with the different patterns of sequence in cardiomyocyte longitudinal orientation indicated in FIG. 10 (type 1 to type 12). A horizontal axis of the graph depicted in FIG. 15 indicates values for angle θ in degree for the different patterns of sequence in cardiomyocyte longitudinal orientation (type 1 to type 12 indicated in FIG. 10) (that is, θ in degree, a difference in angle value of cardiomyocyte longitudinal orientation between adjacent layers). A vertical axis of the graph indicates angle values to represent the ventricular wall torsion. A torsion angle of the ventricle may be presented, for example, by an average of angle values of twist around a z axis which occurs at a finite element at the level of cardiac base of a cardiac structure model 31 in the FIG. 12. A value is positive when a twist occurs in clockwise direction as viewed from the apex, and negative in counter clockwise.

In the analysis data of "torsion of the left ventricular geometry" depicted in FIG. 15, the left ventricular torsions are opposite in direction around an angle of cardiomyocyte longitudinal orientation (θ in degrees) between 20 and 25. The torsions are also nominal with an angle of the cardiomyocyte orientation θ=0 (type 1 in a 3-layers model for the ventricular wall described above) and θ=60 (type 12). A peak in torsion occurs at an angle of the cardiomyocyte orientation θ=35.3 (type 8, a type of cardiomyocyte orientation utilizing a value of a specific bias angle), with a clock-wise rotation at the apex and a counter click-wise rotation at the base as viewed from the apex, a direction consistent with the common observations in physiological human hearts during a diastolic phase. This indicates that the analysis data of simulation (the simulation analysis data) in the cardiac structure model with a composite architecture utilizing a specific bias angle are compatible with a phenomenon of "torsion of the left ventricular geometry" usually observed in control human hearts.

It is well known that a change in extent of the left ventricular torsion (less prominent torsion) is a sensitive indicator for altered ventricular functions. The ventricular compliance also could change in diseased hearts. Thus the analysis data by the simulation part 15 including a change in the left ventricular torsion and a change in the ventricular volume are useful in evaluation of the myocardial and ventricular functions and behaviors such as the ventricular wall compliance, diastolic properties, pump functions as well as the myocardial mechanical properties.

It is also known that two types of hearts with different ventricular hypertrophy, concentric and eccentric hypertrophy, different from control hearts, possess distinctive structural characteristics in cardiomyocyte longitudinal orientation, a volume fraction of connective tissue, connective tissue architecture, etc. The simulation system of cardiac function 10 may input different data (for examples, connective tissue data, myocyte data, construction data, and geometry data described above) which reflect the myocardial tissue characterization in such particular diseased hearts, and precede a simulation. The simulation analysis data may be used to benefit a clarification of pathophysiology in the hearts of ventricular hypertrophy.

FIG. 16 is a table to present an example of input data in a simulation system of cardiac function which uses cardiac structure models individually generated for a control heart and hearts of concentric and eccentric hypertrophy in a cardiac-structure-model construction part 14. The structures and mechanical properties of a composite material composing these different cardiac models reflect the myocardial tissue characteristics distinctive among the three different hearts of control and concentric and eccentric hypertrophy. In the example depicted in FIG. 16 the cardiac structures possess a 5-layers model of the ventricular wall. FIG. 17 is a table to present an example of values for geometry data and values for pressure load which are individually defined in the different cardiac structure models of a control heart and hearts of concentric and eccentric hypertrophy.

As depicted in FIG. 16, in the ventricular wall models comprising a composite material which reflects the myocardial tissue characteristics, a change in longitudinal orientation of reinforcement fiber along the transmural direction of the wall are distinctive between the two types of hypertrophy (concentric and eccentric). Parameters for fiber distribution such as a volume fraction, a diameter, and a center-to-center space noticeably vary among different layers (the first to the fifth layer) in the individual ventricular models for two types of hypertrophy.

Geometry data of the ventricle (parameters for the ellipsoid model), as depicted in FIG. 17, are also distinctive between the two different models of hypertrophy, which reflects different geometries in enlarged ventricle in the two types of hypertrophy.

Thus individual determinants for a cardiac structure model are distinctive between the two types of hypertrophy. All the variable determinants are coordinated into a single system for evaluation of ventricular mechanics in the concentric and eccentric hypertrophy by utilizing the simulation system of cardiac function 10 which uses two different cardiac structure models individually representing particular tissue characteristics of the two types of hypertrophy and simulates a geometry change in the two distinct left ventricular models. It is thus suggested that the simulation system of cardiac function 10 is able to benefit a clarification of different pathophysiology for cardiac diastolic dysfunctions associated with impaired distensibility of the left ventricular wall of two distinctive types of cardiac hypertrophy.

In addition to the benefit in an evaluation of cardiac function and a clarification of cardiac pathophysiology, the simulation system of cardiac function 10 may also be useful in surgical treatments of diseased hearts such as operation as well as medical treatments including a pharmacological therapy. As an example of surgical treatments for diseased hearts, ventricular reconstruction aiming at a reduction in the cavity volume is among optional treatments in diseased hearts with prominent dilation of the left ventricular cavity which possess diastolic dysfunction due to impaired distensibility of the ventricular wall. In such procedures a choice of target shape of the ventricle after reconstruction is crucial to obtain expected improvements in ventricular distensibility. Then it is extremely useful to simulate, based on different data such as pre-operative geometry and prior to the operation, extents of improvement of the left ventricular diastolic properties which are expected in individual cases of available options for post-operative geometry of the left ventricle. Thus the simulation system of cardiac function 10 can be used first to examine various factors of mechanical properties of the diseased heart at the pre-operative condition and then predict and compare expected improvements of the left ventricular diastolic function for individual cases of available options of post-operative left ventricular geometry.

In the field of medical treatment of diseased hearts, especially treatment with pharmacological agents, different medicines are currently under development for treatment of diseased hearts with diastolic heart failure. Among such drugs are those expected to work on connective tissues such as collagen, which is perceived as reinforcement fiber within the cardiac structure model in the present invention. Pharmacological effects of these drugs include changes in amount of collagen fibers within myocardium by manipulating synthesis and/or degradation. Another expected pharmacological effect is inhibition or reversal of biochemical changes of collagen, which accompany alterations in its mechanical properties such as the elastic properties (the Young's modulus). In developing these medicines, it is beneficial first to examine probable involvements of different determinants of ventricular diastolic properties in different types of diseased hearts with diastolic heart failure, then, based on the evaluation of different determinants, to select preferable types of diseased hearts for clinical trials of individual medicines with potential effects on particular determinants. The simulation system of cardiac function 10 is useful for such selection of optimal clinical cases in trial of the medicine under development. In addition, in order to determine in a test tube an extent of a pharmacological effect of medicine on values for the Young's modulus of collagen in the connective tissue, it is crucial to examine the effects of medicine on the composite elastic properties of myocardial tissue and then predict, with additional consideration of other determinants of mechanical properties of the diseased heart, a pharmacological effect of the medicine on a cardiac function in a clinical case. The simulation system of cardiac function 10 is useful to examine the pharmacological effects of medicine, correlating its effects in a test tube and those in clinical cases such as improvements of diastolic properties.

Figure 18:
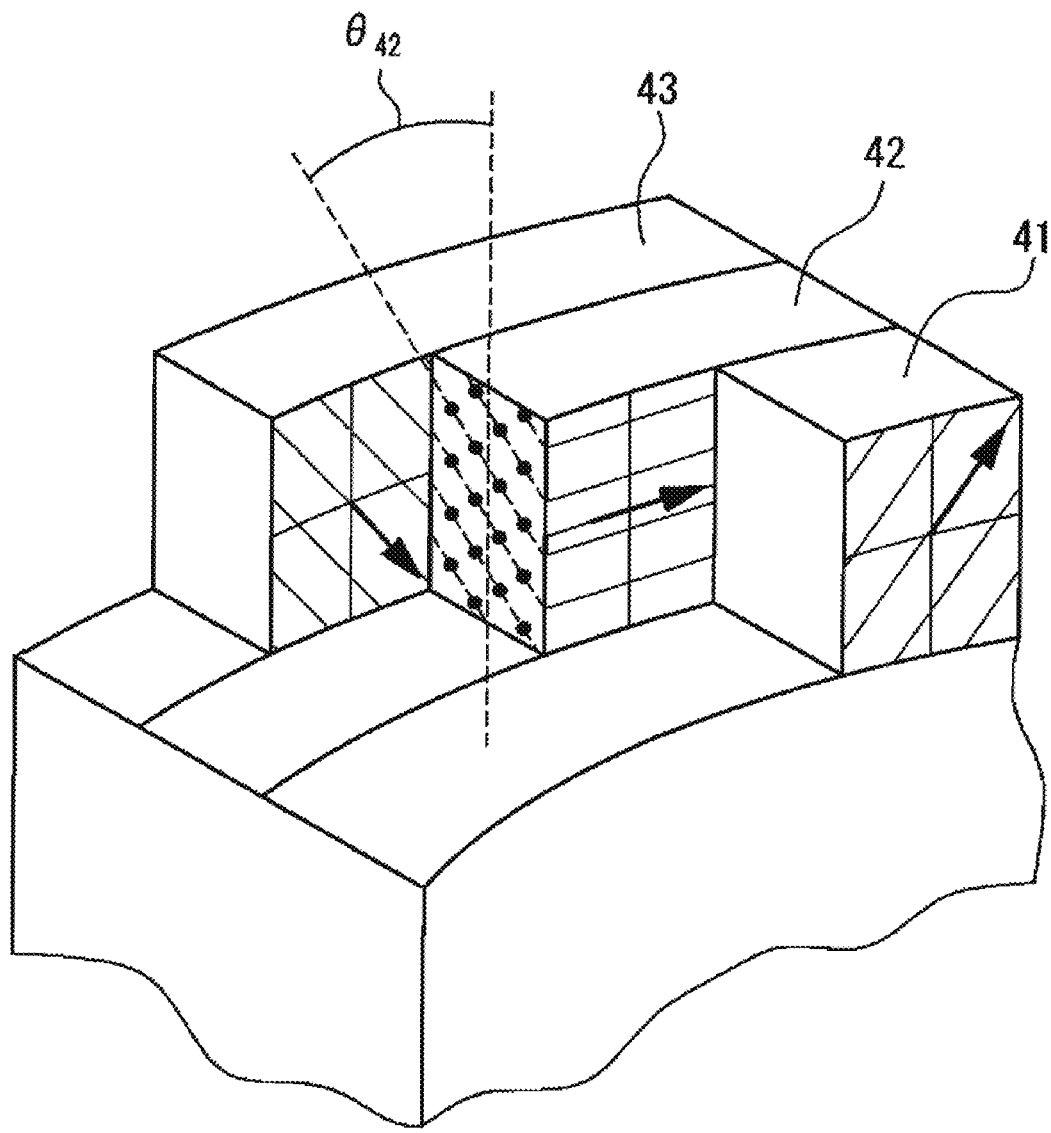
FIG. 18 is a figure to depict the cardiac structure model containing the ventricular wall wherein transmural 3 layers compose a whole thickness of the wall and each layer possesses a particular, uniform distribution of reinforcement fibers.

The cardiac structure model described above in the present embodiment is one example among others in the present invention, but not an exclusive one. For example, as depicted in FIG. 18, the cardiac structure model may contain the ventricular wall wherein transmural 3 layers, 41, 42, and 43, compose a whole thickness of the wall and each layer possesses a particular, uniform distribution of reinforcement fibers. In a case illustrated in FIG. 18, reinforcement fibers within a layer 42 are distributed in a way so that groups of fibers run within individual planes and such planes are arranged in parallel each other. A value for an angle of parallel planes relative to a ventricular tangent, $\theta_{42}$, may be determined as a specific bias angle. With this angle value assigned for the angle $\theta_{42}$, the cardiac structure model is able to reflect a characteristic tissue structure utilizing a specific bias angle which is found in the ventricular wall of actual heart, as described below.

Figure 19A:
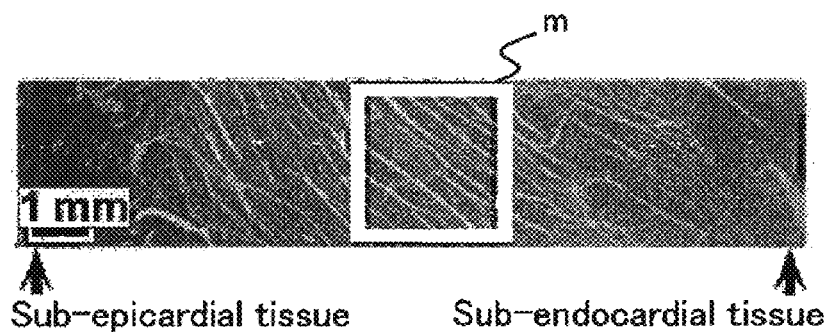
FIG. 19A is a light micrograph from a transmural histology section of the ventricle.
Figure 19B:
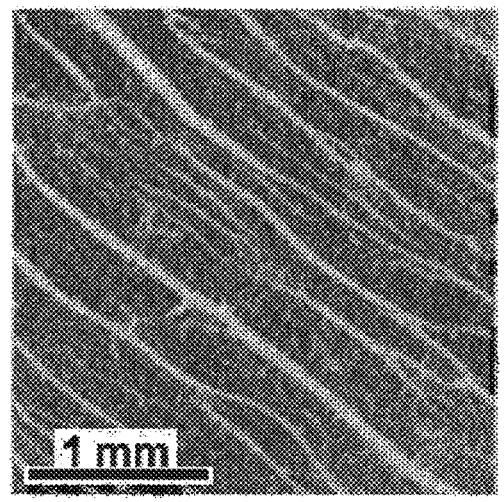
FIG. 19B is a light micrograph of higher magnification from a rectangular area m in the middle of ventricular transmural tissue section depicted in FIG. 19A.

FIG. 19A is a light micrograph from a transmural histology section of the ventricle of actual heart. The right edge of photograph presents the sub-endocardial tissue, and the left edge presents the sub-epicardial tissue of the ventricle. FIG. 19B is a light micrograph of higher magnification from a rectangular area m in the middle of ventricular transmural tissue section depicted in FIG. 19A. As depicted in FIG. 19B the myocardial tissue in the middle layer of ventricular transmural section exhibits cross sections of the bundles of cardiomyocytes which run in parallel. The cross sections of cardiomyocytic bundles, each seen as a flattened layer, compose a laminate architecture. Accordingly clefts between cardiomyocytic bundles (white areas in this photograph), that is, cleavages exhibit a uniform, parallel arrangement along the laminates of cardiomyocytic bundles. This is noted as 'characteristic arrangement of cleavages' in the following description. The connective tissues occupy the open spaces of cleavages. Thus the connective tissue (mainly of perimysium collagen) also exhibits a uniform, parallel arrangement, consistent with the characteristic arrangement of cleavages. A direction of the parallel cleavages depicted in FIG. 19B often makes an angle of a specific bias angle relative to a ventricular tangent in control hearts. Thus the cardiac structure model depicted in FIG. 18 is able to reflect the myocardial tissue structure characterized by such characteristic cleavage architecture.

In an example of the present embodiment the simulation part 15 proceeds a computation with an assumption that directions (angles) of the reinforcement fibers are constant in independent from a change in shape of the ventricular wall due to pressure load. However, in the left ventricle of an actual heart, cardiomyocyte longitudinal orientations slightly change accompanying the ventricular geometry change. Given the change of cardiomyocyte longitudinal orientation in the actual ventricular wall, the simulation part 15 may also proceed a computation with a condition taken into consideration that directions (angles) of the reinforcement fibers change in association with the ventricular geometry change. Such computation provides a simulation with an increased accuracy.

In an example of the present embodiment a simulation of cardiac function does not include a prediction of strength of the myocardial tissue or a heart. However, the material specification input part 11 may also input tension strength, fracture strength, fiber stress etc. of the myocardium, then the simulation system of cardiac function in the present invention is able to provide analysis data which take into consideration the strength of the myocardial tissue or a heart. For example, the simulation part 15 may proceed a computation to provide the analysis data for possible fracture of the myocardial tissue or a heart due to pressure load to the ventricular cavity.

Embodiment 2

The present embodiment relates to a simulation system of cardiac function which facilitates designing a composite material sheet to support a ventricular wall of heart.

A configuration of a simulation system of cardiac function

Figure 20:
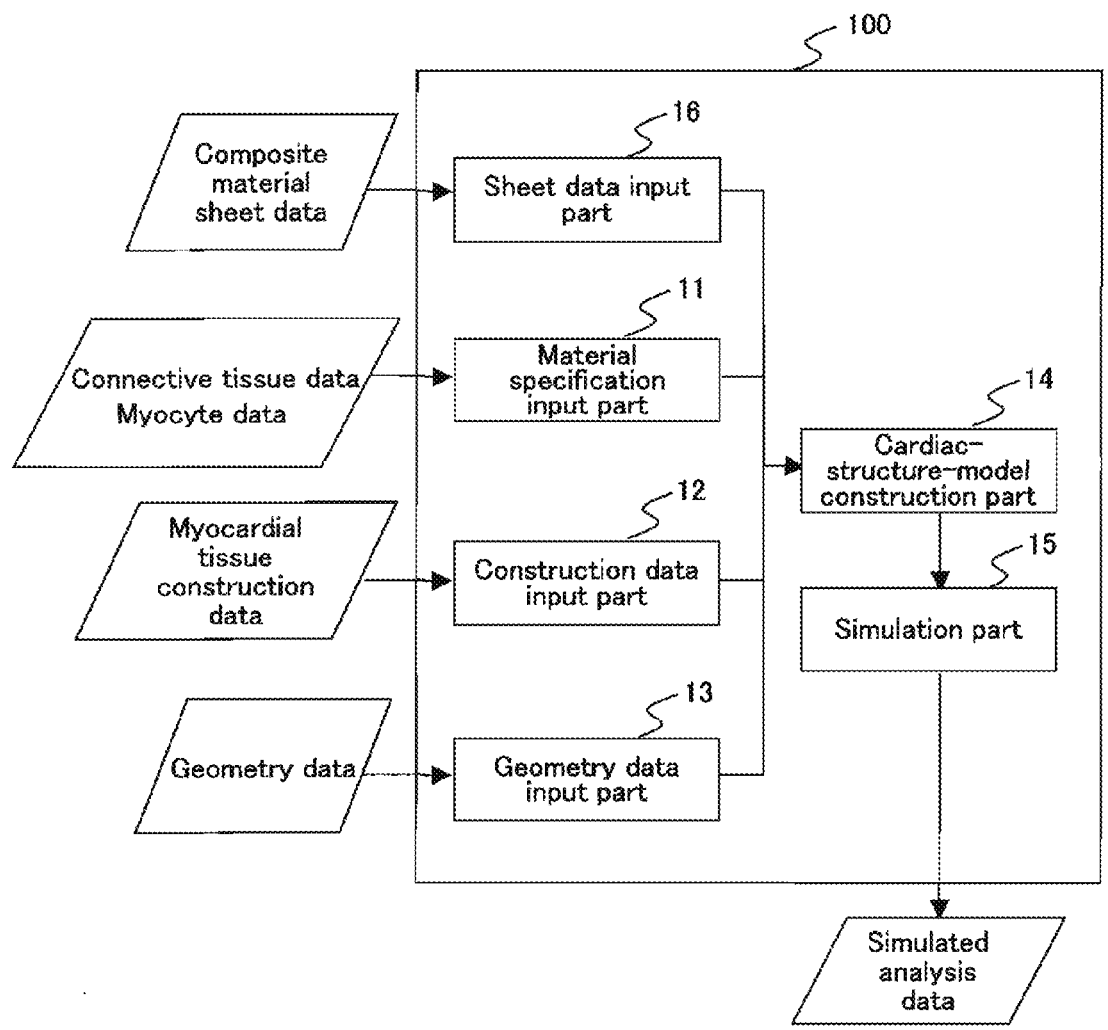
FIG. 20 is a configuration figure of different function blocks in the simulation system of cardiac function.

FIG. 20 is a configuration figure of different function blocks to indicate individual components of the simulation system of cardiac function in the present embodiment. The same function blocks already depicted in FIG. 1 possess the same assigned numbers used in FIG. 1, and detailed descriptions are not provided here. A simulation system of cardiac function 100 depicted in FIG. 20 shares the same simulation system of cardiac function depicted in FIG. 1, but further contains an additional sheet date input part 16.

The sheet date input part 16 is used to input the composite material sheet data presenting a composite material sheet which support all or any part of ventricular wall of a heart. The composite material sheet data contain different data including mechanical properties of reinforcement fiber and matrix within the composite material sheet, orientation of longitudinal alignment of the reinforcement fiber, a shape of the composite material sheet, and other property or configuration of the composite material sheet.

The cardiac-structure-model construction part 14 generates a cardiac structure model made of the continuum of three-dimensional geometry to present a subject heart for simulation analysis wherein the continuum of three-dimensional geometry is configured with composite material sheets presented by the composite material sheet data.

"Composite Material Sheet"

Here provided are descriptions for the composite material sheet to support the ventricular wall of a heart subject for simulation analysis. The composite material sheet used in the present simulation analysis is a sheet made of a unidirectional FRR. As described above in the section of Embodiment 1, based on the comparative examination of the Young' modulus of connective tissue and cardiomyocyte within the myocardial tissue of a heart of non-contracting condition, the myocardial tissue, comprising connective tissue as reinforcement fiber and cardiomyocyte as matrix, possesses material properties consistent with those of directional FRR. Such material properties of non-contracting myocardial tissue consistent with FRR play important roles in maintaining a ventricular geometry as well as diastolic behaviors of the ventricle. Thus the composite material sheet possessing material properties of FRR is beneficial to replace, support, supplement, or repair all or any part of a subject heart in order to improve the cardiac dysfunctions associated with pathologic changes in the myocardial tissue.

Figure 21:
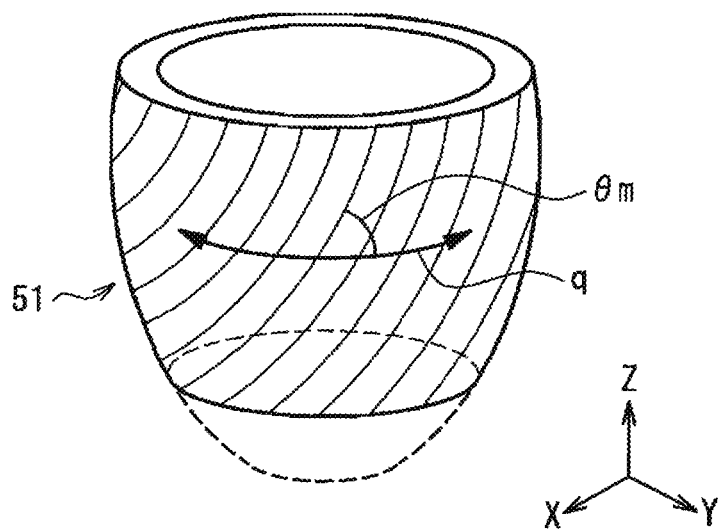
FIG. 21 is an example of the composite material sheet made of a unidirectional FRR lamina (sheet) to support a subject heart.

FIG. 21 depicts an example of the composite material sheet made of a unidirectional FRR lamina (sheet) which serves to support a subject heart. A composite material sheet 51 depicted in the FIG. 21 presents a sack-like contour which possesses openings at both ends of top and bottom and is beneficial to wrap up the heart. The top and bottom openings can vary in diameter so that a contour of the composite material sheet 51 is well adjusted to a shape of the subject heart at the time of attachment. The bottom of a sack-like contour is not necessarily open, but may be closed.

The composite material sheet 51 may present a contour of truncated thick-wall ellipsoid of revolution possessing a longitudinal axis parallel to z axis. The top opening of such composite material sheet 51 may be adjusted in size to fit the base of a subject heart, and the bottom opening may be adjusted in size to fit the apex so that the composite material sheet 51 well attaches the heart.

The composite material sheet 51 may also possess size and contour which would adjust the size and contour of a subject heart at the time of attachment. For example, the top opening of a composite material sheet 51 may present particular size and shape so that the opening would fit the A-V groove of the subject heart.

The composite material sheet 51, when attached to a subject heart, provides varying effects on the cardiac function, depending on different orientations of the reinforcement fiber within the composite in term of geometry of the subject heart. Thus the orientation of reinforcement fiber within a composite material sheet does matter for the effects of the composite sheet. An orientation of the reinforcement fiber can be defined, for example, by an angle value θm determined within a tangential plane of the sheet. The angle valued θm presents an angle relative to an optional reference plane. In this figure, a plane vertical to z-axis is chosen as an example of the reference plane.

An arrow q in FIG. 21 indicates a circumference which presents a cross section of the composite material sheet 51 at the level of the reference plane. Different types of composite material sheet 51 possessing varying values of θm may be prepared, and the ones which well fit a purpose of improving the cardiac dysfunction of subject heart may be selected. For example, different types of the composite material sheet which possess varying values of θm dividing half a circle between −90 to +90 degrees with equal intervals, such as 5 or 10 degrees, may be prepared. Among such a wide variety of composite material sheets a user is able to choose a type of composite material sheet with a value of θm which is optimal for the condition of a subject heart. The cardiac function simulation system 100 in the present invention is able to provide the user useful analysis data in selecting composite material sheets which possess the optimal values of θm.

Figures 22A, 22B:
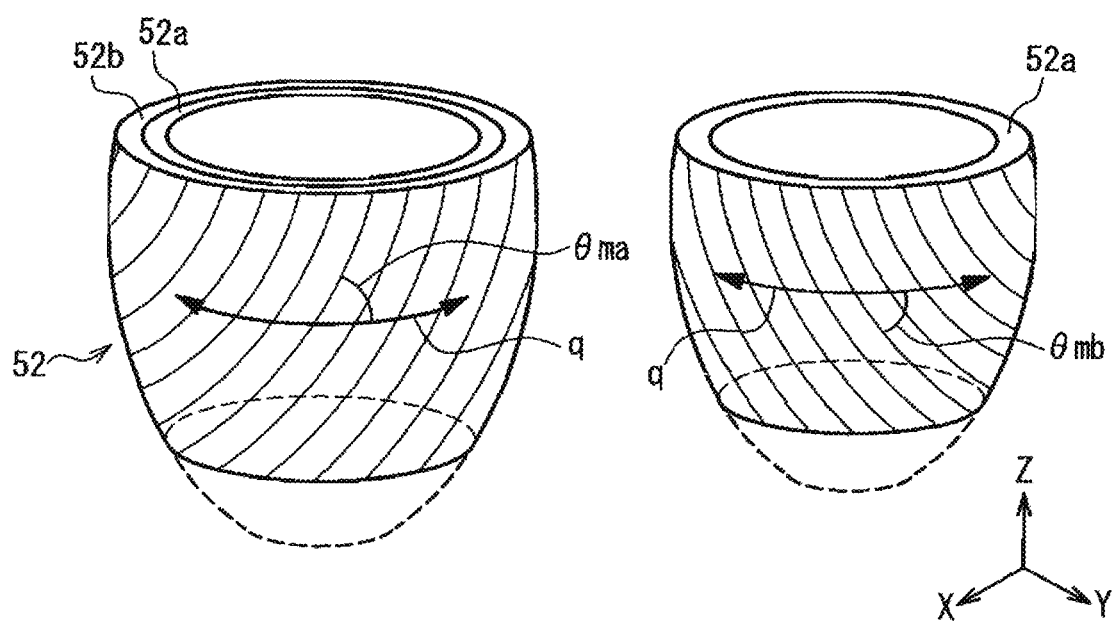
FIG. 22 A depicts an example of the composite material sheet made of a cross-ply laminate with 2 unidirectional FRR laminas (sheets).

FIG. 22A depicts an example of the composite material sheet made of a laminate with two unidirectional FRR laminas (sheets). As depicted in the FIG. 22A an inner layer 52a and an outer layer 52b of the composite material sheet compose the laminate 52 which presents a sack-like contour to warp up a subject heart. As is the case of composite material sheet 51 depicted in FIG. 21, the laminate 52 may also present a sack-like contour which possesses an opening at a bottom end, or may present a contour of truncated thick-wall ellipsoid of revolution possessing a longitudinal axis parallel to z axis depicted in the figure. FIG. 22B depicts only the inner layer 52a of the composite material sheet. An orientation of reinforcement fiber within the outer layer 52b and an orientation of reinforcement fiber within the inner layer 52a may be different (cross-ply lamina).

An orientation of reinforcement fiber within the inner layer 52a or an orientation of reinforcement fiber within the outer layer 52b may be defined by an angle value θma or θmb relative to a reference plane which is vertical to z-axis. The cardiac function simulation system 100 is able to provide useful analysis data to determine the optimal angle values for θma and θmb.

The laminate of composite material sheet does not necessarily comprise two layers of composite material sheets. Laminates comprising any number of composite material sheets more than two layers are able to serve as the laminate of composite material sheet to support a subject heart. FIG. 23A depicts an example of laminate comprising three layers of composite material sheets. The composite material 53 in FIG. 23A is composed of the inner layer 53c, the middle layer 53d, and the outer layer 53e, and all three layers are composite material sheets. FIG. 23B depicts only the middle layer 53d, and FIG. 23C depicts only the inner layer 53c. An orientation of reinforcement fiber within the inner layer 53c, an orientation of reinforcement fiber within the middle layer 53d, and an orientation of reinforcement fiber within the outer layer 53e may be defined by an angle value θmc, θmd (not indicated in the figure because θmd=0), and θme, relative to a reference plane which is vertical to z-axis. The cardiac function simulation system 100 is able to provide useful analysis data to determine the optimal angle values for θmc, θmd, and θme.

Analysis data provided by the cardiac function simulation system 100 are useful to determine whether a single layer of the composite material sheet or a laminate of composite material sheets may better serve to support a subject heart. However, observation of the conditions of individual subject diseased hearts provides somehow predictable clues in selecting preferable composite characteristics of a single layer or a laminate of the composite material sheet. For example, when a defect of the myocardial tissue layer which comprises cardiomyocytic bundles of a particular longitudinal orientation is prominent in the most outer layer of the ventricular wall of a subject heart, a single layer of the composite material sheet containing the reinforcement fibers with the same particular orientation can be preferably chosen as the composite material sheet to support the diseased heart. When a ventricular behavior characterized by torsion similar to that often found in a control heart needs to be reinstalled in a subject diseased heart, there is an option among others to use the laminate of composite material sheets which may present a torsion deformity consistent with the ventricular torsion. In another example of diseased heart of a different condition, when the entire layer of ventricular wall of a particular ventricular area needs to be replaced by the composite material sheet, a preferable option for the material sheet includes multiple layers of composite material sheets with a laminate architecture similar to that of multiple layers of myocardial tissue sheets comprising the ventricular wall of a control heart.

There is a condition of a subject diseased heart wherein a single layer of the composite material sheet is able to improve a cardiac function of the diseased heart yet a large mechanical stress may develop between the attached composite material sheet and the outer surface of ventricular wall if an orientation of the reinforcement fiber within the composite material sheet is much different from a longitudinal orientation of cardiomyocytes within the most outer myocardial tissue layer of the ventricle. Another composite material sheet may be optionally inserted between the attached single layer of composite material sheet and the outer surface of diseased heart to minimize the inter-surface mechanical stress.

The cardiac function simulation system 100 is used to analyze the mechanical characteristics which a subject heart would possess when equipped with the composite material sheet, either of a single layer or a laminate of the sheet, and composite architectures of the sheets are designed so that the diseased heart attached with the composite material sheet would present desired mechanical behaviors. For example, a user has an option to select the number of single layers of the composite material sheet and then, using a cardiac function simulation system 100, analyze mechanical properties of a laminate composed of the selected single layers. A user may also select and use a single layer or a laminate of the composite material sheets with the most beneficial composite architectures to support a subject heart, comparing the mechanical characteristics of different composite material sheets predicted by the cardiac function simulation system 100.

Different materials including steal, alamide, nylon, rayon, carbon fiber, boron fiber, glass fiber, and silica fiber may be used as unidirectional reinforcement fibers of the composite material sheet. Distribution arrangement (cross-sectional distribution) of unidirectional reinforcement fibers within the composite material sheet includes random, square, or hexagonal distribution. Unidirectional reinforcement fibers within the composite material sheet may be either long fibers or short fibers.

Figure 24A:
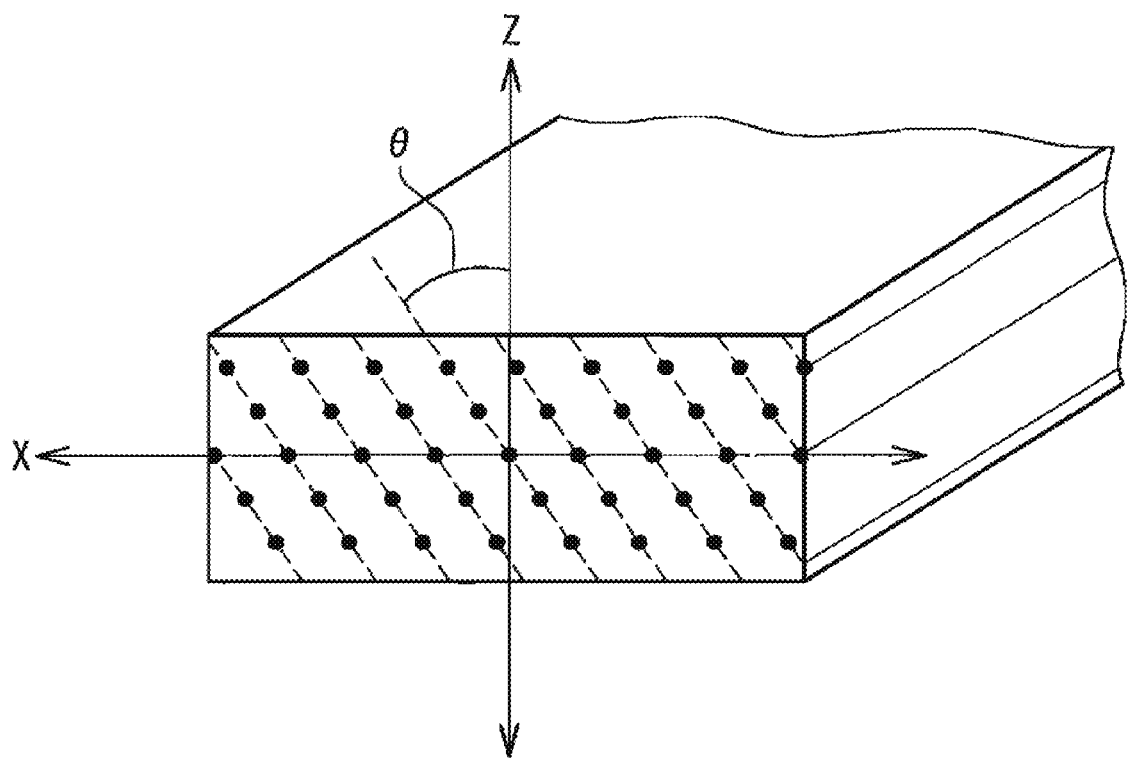
FIG. 24A depicts a cross section of a composite material sheet perpendicular to parallel planes which contain the fabricated reinforcement fibers.
Figure 24B:
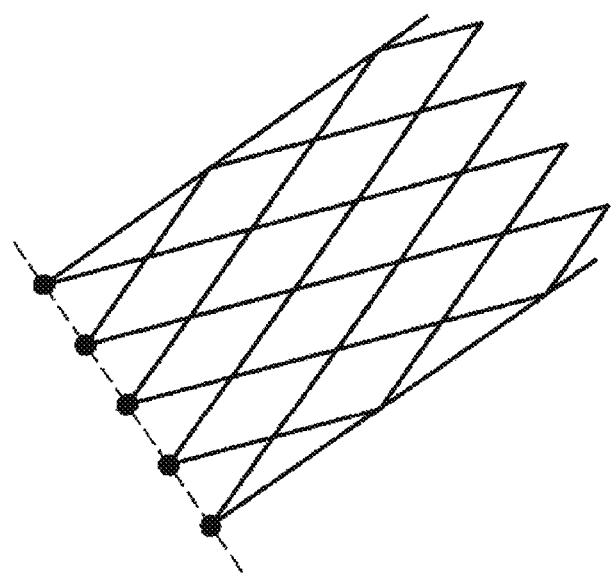
FIG. 24B depicts an example of fabrication of reinforcement fibers within a plane containing the fibers.

Longitudinal alignment or cross-sectional distribution of reinforcement fibers within the composite material sheet is not necessarily parallel in long axis or symmetrical in short axis. For example, as depicted in FIGS. 24A and 24B, reinforcement fibers may be twined in a particular way yet running in a plane, and the planes may be arranged in parallel among the matrix. FIG. 24A depicts a cross section, an x-z plane, of the composite material sheet which is perpendicular to the parallel planes containing twined reinforcement fibers. Dotted lines present cross sections of the individual planes containing twined reinforcement fibers exhibited on the x-z planes. The reinforcement fibers may be arranged in a way so that a value for an angle θ between the dotted lines and z-axis is that of a specific bias angle or its complement.

Among other applications, the composite material sheet indicated in FIG. 24A may be used as the middle layer 53d of composite material 53 depicted in FIG. 23A. The structural arrangement of reinforcement fibers within the middle layer 53d of composite material 53 possesses composite characteristics similar to those of the cleavage architectures of myocardial tissue depicted in FIG. 19. FIG. 24B depicts an example of twining of reinforcement fibers among other options of fabrication designs.

Examples of the composite material sheet wherein the cardiac function simulation system 100 is used for analysis of its composite characteristics are described above referring to FIGS. 21 to 23. Structures of the composite material sheet are not limited to the referred examples. The cardiac function simulation system 100 is also applied to analyze the mechanical characteristics of other structures of the composite sheet such as a rectangular plate of composite material sheet of a single layer or laminate. Different methods such as suture and adherence by tissue adhesives are utilized to equip the composite material sheet to subject hearts. The tissue adhesives include for example polyethylene glycol, fibrin, cyanoacrylate, and combination of bovine serum albumin (BSA) and glutaraldehyde.

An impaired cardiac function in a subject diseased heart may be properly improved by the composite material sheet to support all or any part of the diseased heart, particularly the composite material sheet described above comprising composite sheets which contain unidirectional reinforcement fiber and matrix characterized by a difference in values for the Young modulus one hundred times or more. The composite material sheet with a structure beneficial to improve the cardiac function of a subject heart may be obtained by laminating the composite sheets with characteristic elastic properties of fiber and matrix with an architecture in which orientations of unidirectional reinforcement fiber are optionally defined within individual layers of the laminate. The following is an example of structure of the composite material sheet to improve a cardiac function of a subject diseased heart which is designed utilizing the cardiac function simulation system 100.

An Example of Execution of a Cardiac Function Simulation System

Figure 25:
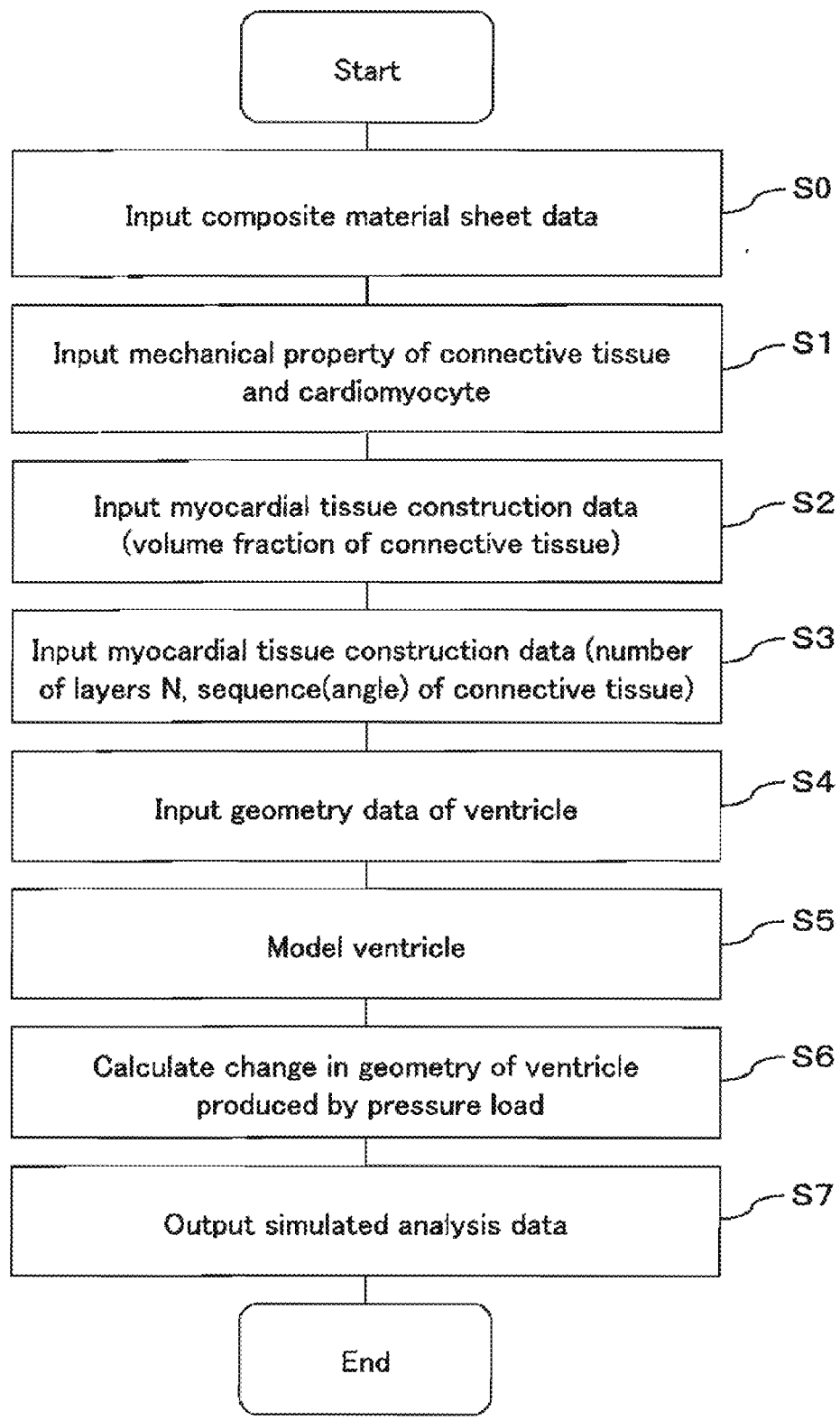
FIG. 25 depicts a flow chart to indicate steps in the execution of the cardiac function simulation system.

The following is a description for example of execution of the cardiac function simulation system 100 in the present embodiment. FIG. 25 depicts a flow chart to indicate steps in the execution of the cardiac function simulation system 100. In this figure the same steps already depicted in FIG. 2 are given the same assigned numbers, and detailed descriptions are not provided. An explanation is provided here in a case of analysis of the geometry change of both the left ventricle of human heart and the laminate 53 depicted in FIG. 23 when the laminate 53 is equipped to the ventricle.

A sheet date input part 16 is used to input composite material sheet data presenting the laminate 53 (step S0). The composite material sheet data, include, for example, a shape of individual composite material sheets comprising the laminate, mechanical properties of reinforcement fiber and matrix within the composite material sheets, and orientations of the reinforcement fiber.

Data to present a shape of the composite material sheet include a thickness of each layer of the three composite material sheets 53c, 53d, and 53e depicted in FIG. 23, and both major and miner radii of an ellipsoid of revolution. A shape of the composite material sheet may be defined according to a shape of a subject heart. For example, the sheet date input part 16 inputs composite material sheet data presenting a shape of the surface of the subject heart. In this case a shape of the composite material sheet which surrounds the heart is consistent with a shape of the outer layer of the heart. The sheet date input part 16 also inputs the information regarding to an attachment position on the heart where the composite material sheet is actually equipped.

Values for the mechanical properties of reinforcement fiber and matrix within the composite material sheet may be optionally determined and inputted by a user. For example, a user may determine optional angle values to input for θmc, θmd, and θme which are defined in individual layers of 53c, 53d, and 53e, respectively. A user examines different combinations of values for angles θmc, θmd, and θme indicating orientations of reinforcement fiber by applying the cardiac function simulation system 100 to each combination, and an optimal combination or combinations of reinforcement fiber orientation can be chosen based on the comparative analysis data of the simulation.

The sheet date input part 16 may be used to input composite material sheet data which are provided by a user. When a composite material sheet is designed by means of a CAD system, the sheet date input part 16 may be used to input composite material sheet data provided as a design data of composite material sheet recorded in a CAD system. The sheet date input part 16 may also be used to input composite material sheet data which have previously been recorded such as measured geometry data of an actual heart.

Composite material sheet data are not limited to data listed above as the examples. Composite material sheet data also include other kinds of data to present detailed architectures of a composite material such as a volume fraction, a diameter, or a center-to-center distance of reinforcement fibers.

Processes at Step S1 to S4 are similar to those indicated in FIG. 2. In Step S5 the cardiac-structure-model construction part 14 generates a cardiac structure model which represents a heart with a ventricle equipped with the composite material sheet 53. The cardiac-structure-model construction part 14 generates a cardiac structure model of continuum of three-dimensional geometry which contains both a ventricle presented by the geometry data input at Step S4 and a composite material sheet to support the ventricle, and determines values for material properties of individual finite elements which comprise the continuum of three-dimensional geometry. For finite elements comprising the equipped composite material sheet, different data such as mechanical properties of reinforcement fiber and matrix of the composite and orientations of reinforcement fiber are determined according to the sheet data inputted in Step S0.

Figure 26:
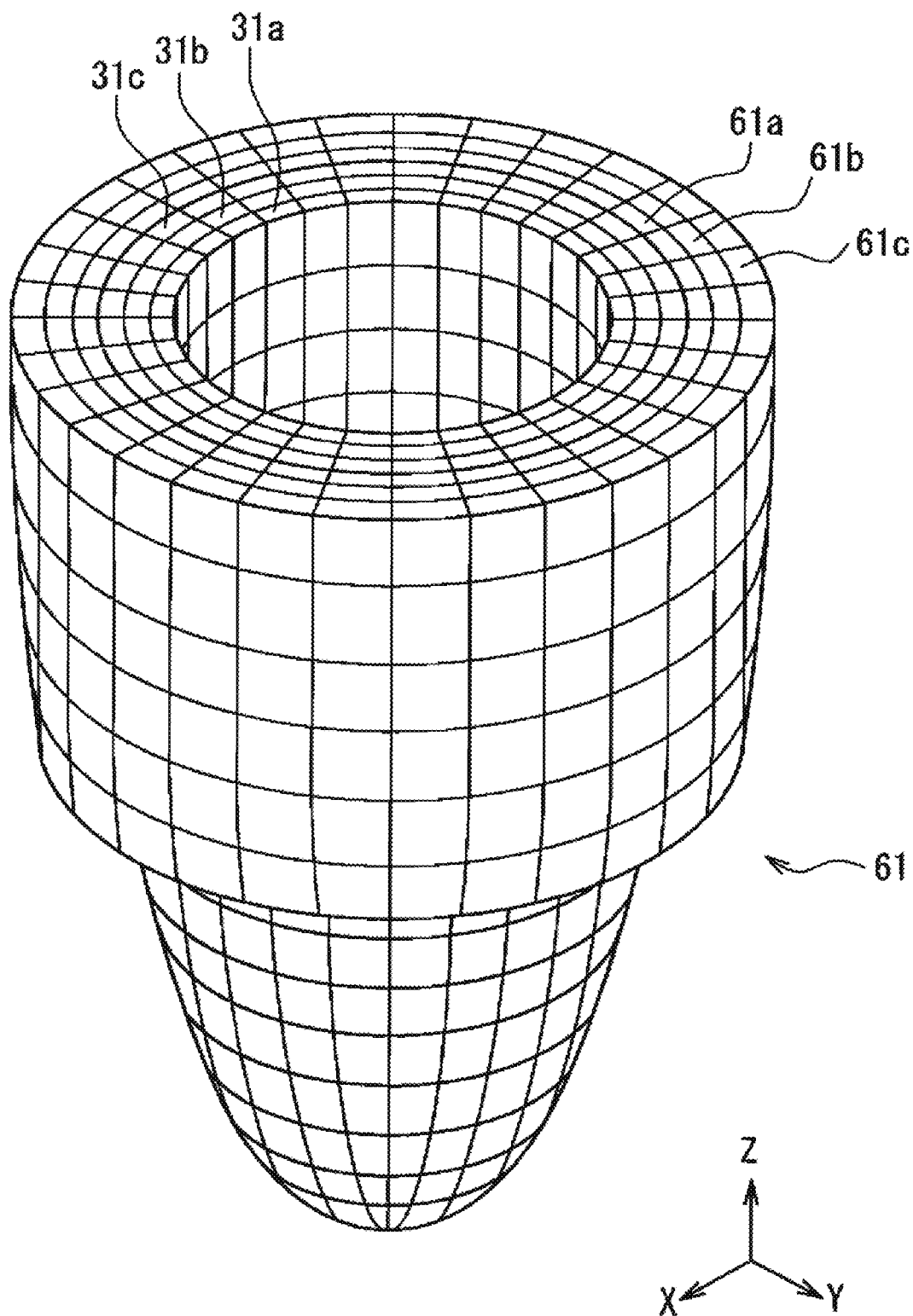
FIG. 26 is a figure to present an example of the cardiac structure model which the cardiac-structure-model construction part 14 generates.

FIG. 26 depicts an example of the cardiac structure model which the cardiac-structure-model construction part 14 generates in Step S5. The inner layer 31a, middle layer 31b, and outer layer 31c of the ventricular wall at the cardiac structure model 61 depicted in FIG. 26 are similar to the inner layer 31a, middle layer 31b, and outer layer 31c at the cardiac structure model 31 depicted in FIG. 12. The cardiac structure model 61 further contains the inner layer 61a, middle layer 61b, and outer layer 61c of a composite material sheet.

Values for mechanical properties of reinforcement fiber and matrix inputted in Step S0 are used for values for mechanical properties of the inner, middle and outer layers, 61a, 61b, and 61c, of the composite material sheet. An angle value θmc, θmd, or θme inputted in Step S0 determines each orientation of reinforcement fiber within the inner, middle, or outer layer, 61a, 61b, or 61c, respectively.

The simulation part 15 determines boundary conditions in finite, element method, proceeds a computation processing using a cardiac structure model generated by the cardiac-structure-model construction part 14, and simulates a change of geometry of the left ventricle which is produced by a cavity pressure load to the internal surface of ventricle (Step S6). Processes in Step S6 and output of simulation analysis data (Step S7) are similar to those in Step S6 and Step S7 indicated in FIG. 2. The simulation analysis data, for example, include changes in shape and dimension of both the ventricular wall and cavity and torsion of the ventricular wall.

A user is able to use the simulation analysis data provided by Step S7 in designing the composite material sheet. An example of the use of simulation data analysis is explained here in a case of the laminate 53 in FIG. 23. The sheet data input part 16 inputs sheet data of composite material including angle values of +37 (a complement of a specific bias angle value), 0, and −37 degrees for θmc, θmd, and θme which individually define reinforcement fiber orientations within the outer, middle, and inner layers, 53e, 53d, and 53e. The cardiac-structure-model construction part 14 generates a cardiac structure model which represents a heart equipped with the laminate 53. The simulation part 15 calculates torsion of the left ventricular wall equipped with the laminate 58 which is produced by a cavity pressure load using the cardiac structure model. The obtained analysis data indicates that the left ventricular wall equipped with the laminate 53 with particular composite characteristics, when an intra-cavity pressure is loaded, would present the torsion which is similar to the ventricular torsion behavior found in association with a cardiac beat of control human heart. Based on such simulation analysis data, a user has an option to use the particular laminate 53 possessing angle values of +37, 0, and −37 degrees of orientations of reinforcement fiber, θmc, θmd, and θme for the composite material sheet product to restore a torsion behavior in a cardiac beat of the subject heart.

Another example of the use of simulation data analysis is explained in the laminate 52 in FIG. 22. In this case the sheet data input part 16 inputs sheet data of composite material including angle values of +54.7 (a specific bias angle value) and −54.7 degrees for θma and θmb which individually define reinforcement fiber orientations within the outer and inner layers 52a and 52b of the laminate 52. The cardiac-structure-model construction part 14 generates a cardiac structure model which represents the ventricle equipped with the laminate 52. The simulation part 15 calculates torsion of the ventricular wall with the laminate 52 which is produced by a cavity pressure load using the cardiac structure model. The obtained analysis data indicates that the ventricular wall equipped with the laminate 52, when an intra-cavity pressure is loaded, would present almost no torsion of the ventricle. Based, on such simulation analysis data, a user has an option to use the particular laminate 52 possessing angle values of +54.7 and −54.7 degrees of orientations of reinforcement fiber θma and θmb for the composite material sheet product which would not cause any additional torsion behavior in a cardiac beat of the subject heart.

In designing composite architectures of the laminate, it is sometimes preferable to determine an orientation of reinforcement fiber of the most inner layer of laminate to agree with, or to be least different from the longitudinal orientation of cardiomyocytes within the most outer layer of myocardial tissue of the ventricular wall of a subject heart. Such composite characteristics of the laminate are preferred so that a local stress on the myocardial tissue of a subject heart would be less prominent at an area adjacent to a boundary to the laminate when it is equipped to the heart. A laminate of the composite material sheet wherein the most inner layer is added to minimize such local stress of myocardial tissue is produced in some cases. In these cases a contribution of the most inner layer to the mechanical properties of whole laminate structure needs to be evaluated. The cardiac function simulation system 100 is available in such prediction of the significance of most inner layer of the laminate.

As another example of a use of the cardiac function simulation system 100, a user is able to examine whether the simulated mechanical behaviors of the ventricle equipped with a laminate are similar to mechanical characteristics of a control heart, and then determine whether the sheet data inputted in a sheet data input part 16 such as a shape or orientations and mechanical properties of reinforcement fiber of the composite material sheet are appropriate ones. The cardiac function simulation system 100, by automatically updating the composite material data sheet data in the sheet data input part 16, may repeat processes of Step S0 to Step S6 until the obtained analysis data such as changes in geometry and dimensions of the ventricular cavity and wall as well as torsion of the ventricular wall would reach a predetermined range. Thus the optimal composite material sheet data are automatically provided.

A practical example of designing a composite material sheet

The following is a description for a practical example of determining architectures of a composite material sheet according to the analysis data of the cardiac function simulation system 100. FIG. 27 is a table depicting examples of orientations and volume fractions of reinforcement fiber which are determined in 3 cardiac structure models of composite material individually representing a control heart, a diseased heart 1, and diseased heart 2. Determined values indicated in the table are provided, for example, according to morphological observations of myocardial tissue. In this example orientations and volume fractions of composite material sheets are determined and these are used to improve cardiac dysfunctions in diseased heart 1 and diseased heart 2, as described below.

First a user inputs determined values for a control heart indicated in FIG. 27 by the construction data input part 12, and the simulation part 15 outputs analysis data such as changes in volume of the ventricular cavity, changes in wall thickness of the ventricular wall, and torsion deformity of the ventricular wall. Then the construction data input part 12 inputs determined values for the diseased heart 1 indicated in FIG. 27, and a sheet data input part 16 inputs sheet data such as orientations and volume fractions of reinforcement fiber for the composite material sheet to be used for the subject diseased heart 1. The simulation part 15 outputs analysis data for the subject diseased heart 1 equipped with the composite material sheet. By comparing the analysis data output for the subject diseased heart 1 equipped with the composite material sheet with the analysis data output for the control heart, the user determines whether the cardiac function of the subject diseased heart 1 equipped with the composite material sheet, would significantly improve. The user repeats a simulation using the cardiac function simulation system 100 with varying sheet data of orientations and volume fractions of reinforcement fiber for a composite material sheet until the returned analysis data for subject heart equipped with the composite material sheet finally indicate a significant improvement in the cardiac function. Thus, the optimal values for orientations and volume fractions of reinforcement fiber are obtained. For example, returned analysis data for the subject heart 1, when equipped with composite material sheet containing reinforcement fiber with an orientation −45 degrees and a volume fraction 0.2, may be most consistent with those for a control heart. In this case it is predicted that the composite material sheet represented by such sheet data, when attached to the diseased hearts, may possibly repair the pathologic changes in orientation of reinforcement fiber within the heart (pathologic changes; orientations of reinforcement fiber in layers 6 and 7 in 7-layers model for the diseased heart 1, as depicted in FIG. 27, are different from those of the control hearts) and accordingly improve the cardiac function.

In an example depicted in FIG. 27, sheet data defined in a 7-layers model for a diseased heart 2 are characterized by an angle range of reinforcement fiber orientation from +45 to −30 degrees (from the endocardial to epicardial side of the ventricular wall). When compared to sheet data of an angle range for a control heart (from +50 to −45 degrees), the sheet data for the diseased heart 2 indicate that both the reinforcement fibers with an angle +50 degrees within the sub-endocardial layer of ventricle and the reinforcement fiber with an angle value −45 within the sub-epicardial layer of ventricle disappear in the diseased heart 2. In order to design a composite material sheet to supplement the disappeared reinforcement fibers in a diseased heart, a user may use a cardiac function simulation system and proceed a simulation of cardiac function of the diseased heart 2 when a composite material sheet such as that of a single layer or multiple-layers structure (for example, 2-5 layers) is equipped. For example, the returned analysis data for the diseased heart 2, when equipped with a composite material sheet of 3-layers structure containing reinforcement fibers with an orientation −45 degrees, 0 degree, and +50 degrees for the inner, middle, and outer layers, and a volume fraction 0.2 for all three layers, may be most consistent with those for the control heart. In this case a composite material sheet of the 3-layers structure possessing such sheet data is considered desirable.

As described above, the simulation system of cardiac function 100 in the present embodiment is able to assist to design an appropriate composite material sheet to support all or any part of the ventricle of diseased heart.

The present embodiment relates to a composite material sheet which supports all or any part of heart. The composite material sheet in the present execution structure comprises a lamina or a laminate of thin sheet made of a composite material containing unidirectional reinforcement fiber and matrix. The composite material is characterized by a value for the Young' modulus of the reinforcement fiber as large as one hundred times or more of a value for the Young' modulus of matrix.

Architectural characteristics of the composite material sheet including a structure, a total number of the sheet, and orientations of reinforcement fibers within individual composite material thin sheets are determined based on shapes and diseased conditions of individual subject hearts. For example, as indicated in the embodiment 2, the architecture of the composite material sheet can be determined by utilizing the simulation system of cardiac function 100. In the present embodiment, a material which comprises the composite material sheet is mainly described.

A FRR is one example of the composite material which possesses a value for the Young' modulus of the reinforcement fiber as large as one hundred times or more of a value for the Young' modulus of matrix. A FRR contains a matrix of rubber material and a reinforcement fiber indicated in the embodiment 2.

A biocompatible rubber material may be used as a rubber material of the composite material sheet. A biocompatible material is a material biologically inactive so that surrounding tissues do not suffer from any damage by possible processes such as an excessive or harmful rejection reaction, inflammation, infarction or necrosis. Examples of a biocompatible rubber material include a rubber material which is free of, or less likely evoking a latex allergy reaction. Among such biocompatible rubber materials are polyurethane rubber, polyurethane thermoplastic rubber, deproteinized rubber, and silicon rubber.

An electroactive polymer such as a dielectric elastomer is also used as a rubber material of the composite material sheet. The electroactive polymer facilitated with electrodes is utilized as an actuator to replace, supplement, or improve a systolic function of a ventricle of a heart. For example, an electroactive polymer of a cylinder shape mimicking a cardiomyocyte which possesses both longitudinal and cross-sectional axes shape and is attached with electrodes may be used as a rubber material of the composite material sheet. Then a composite material sheet is made by assembling within a sheet the electroactive polymer materials with such cylindrical contour in parallel arrangement along their longitudinal axes. In this particular sheet, materials to maintain a cylindrical contour of the electroactive polymer, materials to support the unidirectional arrangement of individual electroactive polymer material, or materials comprising the electrodes may serve as reinforcement fiber elements within the composite material sheet.

A cardiomyocyte for implantation produced by a bioengineering technique, as another example for FAR, may also be used as a rubber material of the composite material sheet. For example, the implantation cardiomyocytes are produced by cell culture technique using different cells such as an embryonic stem cell and a bone marrow-derived stem cell. Connective tissue fibers for implantation produced by a bioengineering technique may also be used as reinforcement fiber of the composite material sheet. Such connective tissue fibers for implantation include commercial collagen for a medical use, collagen sponge for cell culture, and artificial collagen.

For example, a cardiomyocyte for implantation which possesses a cardiomyocyte-like contour with both longitudinal and cross-sectional axes and polarity, as observed in the myocardial tissue, may be used as a rubber material of the composite material sheet. The composite material sheet may contain a number of such cardiomyocytes of a cylindrical shape which run in parallel along their longitudinal axes. The composite material sheet containing implanted cardiomyocytes with unidirectional arrangement is able to be made by utilizing existing bioengineering methods to produce a cell sheet (see a reference listed below). A material for reinforcement fiber of the composite material sheet may include a surface material used in cell culture (a collagen membrane for cell culture, for example) which is used in a bioengineering production of a sheet containing implanted cardiomyocytes with unilateral alignment.

(Reference) Furuta A. et al. Pulsatile cardiac tissue grafts using a novel three-dimensional cell sheet manipulation technique functionally integrates with the host heart, in vivo. Circulation Research 17; 98:705-712, 2006 (March). U.S.A. American Heart Association, Inc.

The present invention is useful as a simulation system of cardiac function wherein a simulation of cardiac function can be developed using a cardiac structure model appropriately reflecting morphological and mechanical properties of cardiomyocyte and connective tissue within the actual myocardial tissue. The present invention is also useful as a composite material sheet which is compatible with the morphological and mechanical properties of cardiomyocyte and connective tissue within the actual myocardial tissue.

The invention claimed is:

1. A simulation system of cardiac function comprised of at least one computer to simulate a change in ventricular geometry by utilizing a cardiac structure model which represents a heart made of the myocardial tissue comprising both myocyte and connective tissue as continuum data of a composite material containing both matrix and reinforcement fiber, comprising:
    a material specification input part that inputs both connective tissue data representing mechanical property of the connective tissue within the myocardial tissue and myocyte data representing mechanical property of the myocyte within the myocardial tissue, and stores the connective tissue data and the myocite data into a memory;
    a geometry data input part that inputs geometry data of three-dimensional geometry of all or any part of the heart and stores the geometry data into the memory;
    a cardiac-structure-model construction part that generates, by a processor, the cardiac structure model that represents the three-dimensional geometry as an assembly of finite elements, sets a mechanical property and a direction of the reinforcement fiber with respect to at least one of the finite elements and sets a mechanical property of the matrix with respect to at least one of the finite elements, wherein the mechanical property represented by the myocyte data is set as a mechanical property of the matrix and the mechanical property represented by the connective tissue data is set as a mechanical property of the reinforcement fiber; and
    a simulation part that determines a boundary condition and calculates a change in geometry of the heart represented by the cardiac structure model under a pressure load according to the boundary condition.

2. A simulation system of cardiac function according to claim 1 wherein the material specification input part inputs the connective tissue data including a value for the Young's modulus of the connective tissue and the myocyte data including a value for the Young's modulus of the myocyte, and
    the value for the Young's modulus of the connective tissue is as large as one hundred times or more of the value for the Young's modulus of the myocyte.

3. A simulation system of cardiac function according to claim 1, wherein the cardiac-structure-model construction part generates the cardiac structure model that represents the three-dimensional geometry as the assembly of finite elements and sets the mechanical property of the matrix made of rubber with respect to the at least one of the finite elements and the mechanical property of the unidirectional reinforcement fiber with respect to the at least one of the finite elements, and
    the mechanical property of the unidirectional reinforcement fiber is defined by the property of the connective tissue represented by the connective tissue data and the mechanical property of the matrix is defined by the property of myocyte represented by the myocyte data within the cardiac structure model.

4. A simulation system of cardiac function according to claim 1 further comprising a construction data input part that inputs myocardial tissue construction data including a volume fraction of the connective tissue within the myocardial tissue;
    wherein the cardiac-structure-model construction part determines a volume fraction of the reinforcement fiber within the composite material composing the cardiac structure model based on the volume fraction of the connective tissue within the myocardial tissue.

5. A simulation system of cardiac function according to claim 1 further comprising a construction data input part that inputs myocardial tissue construction data including cell diameter of the myocyte;
    wherein the cardiac-structure-model construction part determines a center-to-center distance of the reinforcement fibers within the composite material composing the cardiac structure model based on the cell diameter of the myocyte.

6. A simulation system of cardiac function according to claim 1 further comprising a construction data input part that inputs myocardial tissue construction data including a value for volume fraction of the connective tissue within myocardial tissue and a value for cell diameter of the myocyte;
    wherein cardiac-structure-model construction part determines diameter of the reinforcement fiber within the composite material composing the cardiac structure model based on both the value for the volume fraction of the connective tissue within the myocardial tissue and the value for the cell diameter of the myocyte.

7. A simulation system of cardiac function according to claim 1 further comprising a construction data input part that inputs myocardial tissue construction data including data representing an orientation of longitudinal alignment of the cardiomyocyte;
    wherein the cardiac-structure-model construction part generates the cardiac structure model that represents the three-dimension geometry as the assembly of finite elements including groups of finite elements that compose laminated, curved sheets, respectively and sets orientations of longitudinal alignment of the reinforcement fiber in each of the laminated, curved sheets of the composite material composing the cardiac structure model according to the myocardial tissue construction data.

8. A simulation system of cardiac function according to claim 7 wherein the cardiac-structure-model construction part defines a ventricular wall of the heart that is composed of N (N is an odd number) layers of the curved sheets of the composite material, and the orientation of longitudinal alignment of reinforcement fiber in the central layer among the N layers of curved sheets is defined by the fiber orientation of ventricular circular muscle of the heart.

9. A simulation system of cardiac function according to claim 7 wherein the cardiac-structure-model construction part defines orientations of longitudinal alignment of the reinforcement fiber in individual curved sheets so that the orientations are in-plane within each curved sheet and yet vary among different curved sheets.

10. A simulation system of cardiac function according to claim 9 wherein the material specification input part inputs value for Young's modulus of the myocyte as the myocyte data and the value for the Young's modulus of connective tissues as large as one hundred times or more of the value for the Young's modulus of the myocyte as the connective tissue data, and
    the cardiac-structure-model construction part defines the orientations of longitudinal alignment of the reinforcement fiber so that the orientations differ by angle value of a specific bias angle or its complement between at least one pair of adjacent curved sheets.

11. A simulation system of cardiac function according to claim 1 further comprising a sheet data input part that inputs sheet data representing a composite material sheet to support all or any part of the heart and including mechanical properties of a reinforcement fiber and a matrix within the composite material sheet, orientation of longitudinal alignment of the reinforcement fiber, and a shape of the composite material sheet;
wherein the cardiac-structure-model construction part generates a cardiac structure model representing a continuum of the three-dimensional geometry represented by the geometry data configured with the composite material sheets characterized by the sheet data.

12. A simulation method of cardiac function using at least one sufficiently programmed computer to simulate a change in ventricular geometry by computation wherein the simulation method utilizes a cardiac structure model to represent a heart made of the myocardial tissue comprising both myocyte and connective tissues as continuum data of a composite material containing matrix and reinforcement fiber, comprising:
inputting connective tissue data representing mechanical property of the connective tissue within the myocardial tissue ad myocyte data representing mechanical property of the myocyte within the myocardial tissue and storing the connective tissue data and the myocite data into a memory;
inputting geometry data of three-dimensional geometry of all or any part of the heart and storing the geometry data into the memory;
generating the cardiac structure model that represents the three-dimensional geometry as assembly of finite elements, setting a mechanical property and a direction of the reinforcement fiber with respect to at least one of the finite elements and setting a mechanical property of the matrix with respect to at least one of the finite elements, wherein the mechanical property represented by the myocyte data is set as a mechanical property of the matrix and the mechanical property represented by the connective tissue data is set as a mechanical property of the reinforcement fiber; and
determining a boundary condition and calculating a change in geometry of the heart represented by the cardiac structure model under a pressure load according to the boundary condition.

13. A non-transitory recording medium that stores a simulation program of cardiac function by directing a computer to execute a simulation of a change in ventricular geometry wherein the simulation program utilizes a cardiac structure model to represent a heart made of the myocardial tissue comprising both myocyte and connective tissue as continuum data of a composite material containing matrix and reinforcement fiber, the simulation program directs the computer to execute:
a computation processing to input both connective tissue data representing mechanical property of the connective tissue within myocardial tissue and myocyte data representing mechanical property of the myocyte within the myocardial tissue;
a computation processing to input geometry data of three-dimensional geometry of all or any part of the heart;
a cardiac-structure-model construction processing to generate the cardiac structure model that represents the three-dimensional geometry as an assembly of finite elements, set a mechanical property and a direction of the reinforcement fiber with respect to at least one of the finite elements and set a mechanical property of the matrix with respect to at least of one of the finite elements, wherein the mechanical property represented by the myocyte data is set as a mechanical property of the matrix and the mechanical property represented by the connective tissue data is set as a mechanical property of the reinforcement fiber; and
a computation processing to determine a boundary condition and calculate a change in geometry of the heart represented by the cardiac structure model under a pressure load according to the boundary condition.

* * * * *